US006486193B2

(12) United States Patent
Flynn

(10) Patent No.: US 6,486,193 B2
(45) Date of Patent: Nov. 26, 2002

(54) 3-SUBSTITUTED PYRROLIDINES USEFUL AS INHIBITORS OF MATRIX METALLOPROTEINASES

(75) Inventor: Gary A. Flynn, Tucson, AZ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/815,868

(22) Filed: Mar. 23, 2001

(65) Prior Publication Data

US 2002/0037859 A1 Mar. 28, 2002

Related U.S. Application Data

(63) Continuation-in-part of application No. 09/465,744, filed on Dec. 17, 1999.
(60) Provisional application No. 60/172,223, filed on Dec. 31, 1998.

(51) Int. Cl.[7] .................... C07D 207/09; C07D 403/12; A61P 29/00; A61K 31/402

(52) U.S. Cl. ....................... 514/423; 514/357; 546/337; 548/537

(58) Field of Search ................................. 514/357, 423; 546/337; 548/537

(56) References Cited

U.S. PATENT DOCUMENTS

| | | | |
|---|---|---|---|
| 4,500,467 A | 2/1985 | Kubinyi et al. | |
| 4,880,781 A | 11/1989 | Hester et al. | |
| 5,147,865 A | 9/1992 | Häbich et al. | |
| 5,311,942 A | 6/1994 | Rapoport et al. | |
| 5,340,801 A | 8/1994 | Ewing et al. | |
| 5,340,802 A | 8/1994 | Shiosaki et al. | |
| 5,424,425 A | 6/1995 | Flynn et al. | |
| 5,439,918 A | 8/1995 | deSolms et al. | |
| 5,462,964 A | 10/1995 | Fevig et al. | |
| 5,491,143 A | 2/1996 | Flynn et al. | |
| 5,605,926 A | 2/1997 | Häbich et al. | |
| 5,661,161 A | 8/1997 | Anthony et al. | |
| 5,731,306 A | 3/1998 | Flynn et al. | |
| 5,932,567 A | 8/1999 | Werner et al. | |
| 5,994,312 A | * 11/1999 | Montana et al. | ............... 514/19 |

FOREIGN PATENT DOCUMENTS

| | | |
|---|---|---|
| EP | 0173481 | 3/1986 |
| EP | 0486478 | 5/1992 |
| EP | 0805147 | 11/1997 |
| WO | 8904833 | 6/1989 |
| WO | 9115121 | 3/1991 |
| WO | 9204370 | 3/1992 |
| WO | 9521839 | 1/1995 |
| WO | 9625426 | 2/1996 |
| WO | 9677209 | 4/1996 |
| WO | 9812211 | 1/1998 |
| WO | 8806890 | 9/1998 |
| WO | 9853817 | 12/1998 |

OTHER PUBLICATIONS

Chang, F et al, 1997, Cancer, 80(12, Suppl.), 2347–2353.*
Chapman et al.,*J. Med. Chem.* vol. 36, No. 26, 4293–4301 (1993).
Beckett et al., *DDT* vol. 1, No. 1, 16–26 (1996).
S.S. McCachren, *Arthritis Rheum.* vol. 34, No. 9, 1085–1093 (1991).
Emonard et al., *Cell Molec. Biol.* 36, (2) 131–153 (1990).
Birkedal–Hansen, H., *J. Oral Pathol.* 17:, 445–451 (1988).
L.M. Matrisian, *Trends Genet.* vol. 6, No. 4, 121–125 (1990).
Murphy et al., *FEBS Lett.* 289, 4–7 (1991).
L.M. Matrisian, *Bioessays* vol. 14, No. 7, 455–463 (1992).
Schwartz et al., *Cancer* vol. 73, No. 1, 22–27 (1994).
Bernhard et al., *Proc. Natl. Acad. Sci.* USA, vol. 91, 4293–4597 (1994).
Zucker et al., *Cancer Res.* 53, 140–146 (1993.
Chirivi et al., *Int. J. Cancer* 58, 460–464 (1994).
Montgomery et al., *Cancer Res.* 54, 5467–5473 (1994).
Beeley et al., *Curr. Opin. Ther. Patents*, 4(1):, 7–16 (1994.
Hasty et al., *Arthr. Rheum.* vol. 33, No. 3, 388–397 (1990).
Murphy et al., Biochem J. 248, 265–268 (1987).
Gearing, et al., Nature vol. 370, 555–557 (1994).
Mohler et al., *Nature* 370, 218–220, (1994).
McGeehan et al., *Nature* 370, 558–561 (1994).
Wahl et al., *Annual Reports in Medicinal Chemistry* 25, 177–184 (1989).
Shapiro et al., *Science*, 277, 2002 (1997).
Henney et al., *Proc. Natl. Acad. Sci.*, USA, vol. 88, 8154–8158 (1991).
Burns et al., *Invest. Opthalmol. and Visual Sci.* 30, No. 7, 1569–1575 (1989).
Overall et al., *J. Periodontal Res.* 22, 81–88 (1987).
Miyazaki et al., *Nature* vol. 362, 839–841 (1993).

(List continued on next page.)

*Primary Examiner*—Joseph K. McKane
*Assistant Examiner*—Andrea D. Small
(74) *Attorney, Agent, or Firm*—Julie Anne Knight

(57) ABSTRACT

The present invention provides novel 3-substituted pyrrolidines of the formula

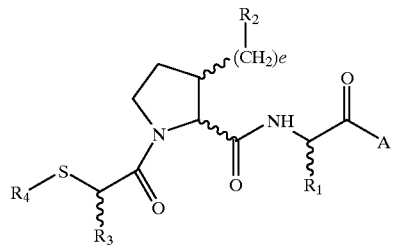

useful in as inhibitors of matrix metallo-proteinases (MMPs). Pharmaceutical compositions containing said compounds as well as methods of treating disease states responding to inhibition of matrix metalloproteinase are also claimed herein.

33 Claims, No Drawings

OTHER PUBLICATIONS

Evans et al., *J. Am. Chem. Soc.*, vol. 112, No. 10, 4011–4030 (1990).
Ikegami et al., *Tetrahedron*, vol. 44, No. 17, 5333–5342 (1988).
Oppolzer et al., *Tet. Lets.*, vol. 30, No. 44, 6009–6010 (1989).
R.M. Williams, *Synthesis of Optically Active α–Amino Acids* (Pergamon Press, Oxford 1989.
M.J. O'Donnell ed.: *α–Amino Acid Synthesis, Tetrahedron Symposia* in print, No. 33, *Tetrahedron* 44, No. 17 (1988).
Schöllkopf, *Pure Appl. Chem.* vol. 55, No. 11, 1799 (1983).
U. Hengartner et al., *J. Org. Chem.*, vol. 44, No. 22, 3748–3752 (1979).
O'Donnell et al., *Tet. Lets.*, 2641–2644 (1978).
O'Donnell et al., *Tet. Lets.*, vol. 23, 4255–4258 (1982).
O. Donnell et al., *J. Am. Chem. Soc.*, vol. 110, 8520–8525 (1988).
Rink, *Tet. Let.*, 28, 3787 (1987).
Sieber, *Tet. Let.*, 28, 2107 (1987).
K.S. Lam, *Chem. Rev.*, 97, 411–448 (1997).
J. Kapoor, *J. Pharm. Sci.*, 59, 1–27 (1970).
Roques et al., *J. Med. Chem.*33, 2473–2481 (1992).
Compagnone, R.S. and H. Rapoport, *J. Org. Chem.*, 51, 1713–1719 (1986).
Overberger, C.G. and I. Cho, *J. Org. Chem.*, vol. 33, No. 8, 3321–3322 (1968).
Pfister et al., *J. Am. Chem. Soc*, vol. 71, 1096–1100 (1949).
Harmon et al., *J. Org. Chem.*, 38, 11–16 (1973).
Okada et al., *J. Biol. Chem.* vol. 261, No. 30, 14245–14255 (1986).
Knight et al., *FEBS Lett.* vol. 96, 263–266 (1992).
Shapiro et al., *J. Biol. Chem.*, vol. 268, 23824–23829 (1993).
Sawayama et al., *Chem. Pharm. Bull.*, 38(2), 529–521 (1990).
Takama et al., *J. Pharm. Pharmacol.*, 45, 1003–1005 (1993).
Yiotakis et al., *Eur. J. Biochem.*, 172, 761–766 (1988).
Slusarchyk et al, *Biorganic & Medicinal Chemistry Letters*, vol. 5, No. 7, pp. 753–758, Jun. 4, 1995.
Muller et al., *J. Biol. Chem.*, vol. 378 (12), pp. 1475–1480, Dec. 1997.
Chang, F. et al, 1997, *Cancer*, 80(12, Suppl.), 2347–2353.

* cited by examiner

3-SUBSTITUTED PYRROLIDINES USEFUL AS INHIBITORS OF MATRIX METALLOPROTEINASES

This application is a continuation-in-part of U.S. application Ser. No. 09/465,744, filed Dec. 17, 1999, now abandoned, which claims the benefit of U.S. Provisional Application No. 60/172,223, filed Dec. 31, 1998.

BACKGROUND OF THE INVENTION

The matrix metalloproteinases (MMPs) are a family of zinc containing endopeptidases which are capable of cleaving large biomolecules such as the collagens, proteoglycans and gelatins. Expression is upregulated by pro-inflammatory cytokines and/or growth factors. The MMP's are secreted as inactive zymogens which, upon activation, are subject to control by endogenous inhibitors, for example, tissue inhibitor of metalloproteinases (TIMP) and $\alpha_2$-macroglobulin. Chapman, K. T. et al., *J. Med. Chem.* 36, 4293–4301 (1993); Beckett, R. P. et al., *DDT* 1, 16–26 (1996). The characterizing feature of diseases involving the enzymes appears to be a stoichiometric imbalance between active enzymes and endogenous inhibitors, leading to excessive tissue disruption, and often degradation. McCachren, S. S., *Arthritis Rheum.* 34, 1085–1093 (1991).

The discovery of different families of matrix metalloproteinase, their relationships, and their individual characteristics have been categorized in several reports. Emonard, H. et al., *Cell Molec. Biol.* 36, 131–153 (1990); Birkedal-Hansen, H., *J. Oral Pathol.* 17, 445–451 (1988); Matrisian, L. M., *Trends Genet.* 6, 121–125 (1990); Murphy, G. J. P. et al., *FEBS Lett.* 289, 4–7 (1991); Matrisian, L. M., *Bioessays* 14, 455–463 (1992). Three groups of MMPs have been delineated: the collagenases which have triple helical interstitial collagen as a substrate, the gelatinases which are proteinases of denatured collagen and Type IV collagen, and the stromelysins which were originally characterized as proteoglycanases but have now been identified to have a broader proteolytic spectrum. Examples of specific collagenases include fibroblast collagenase (MMP-1), neutrophil collagenase (MMP-8), and collagenase 3 (MMP-13). Examples of gelatinases include 72 kDa gelatinase (gelatinase A; MMP-2) and 92 kDa gelatinase (gelatinase B; MMP-9). Examples of stromelysins include stromelysin 1 (MMP-3), stromelysin 2 (MMP-10) and matrilysin (MMP-7). Other MMPs which do not fit neatly into the above groups include metalloelastase (MMP-12), membrane-type MMP (MT-MMP or MMP-14) and stromelysin 3 (MMP-11). Beckett, R. P. et al., supra.

Over-expression and activation of MMPs have been linked with a wide range of diseases such as cancer; rheumatoid arthritis; osteoarthritis; chronic inflammatory disorders, such as emphysema and smoking-induced emphysema; cardiovascular disorders, such as atherosclerosis; corneal ulceration; dental diseases such as gingivitis and periodontal disease; and neurological disorders, such as multiple sclerosis. For example, in adenocarcinoma, invasive proximal gastric cells express the 72 kDa form of collagenase Type IV, whereas the noninvasive cells do not. Schwartz, G. K. et al., *Cancer* 73, 22–27 (1994). Rat embryo cells transformed by the Ha-ras and v-myc oncogenes or by Ha-ras alone are metastatic in nude mice and release the 92 kDa gelatinase/collagenase (MMP-9). Bernhard, E. J. et al., *Proc. Natl. Acad. Sci.* 91, 4293–4597 (1994). The plasma concentration of MMP-9 was significantly increased (P <0.01) in 122 patients with gastrointestinal tract cancer and breast cancer. Zucker, S. et al., *Cancer Res.* 53, 140–146 (1993). Moreover, intraperitoneal administration of batimastat, a synthetic MMP inhibitor, gave significant inhibition in the growth and metastatic spread and number of lung colonies which were produced by intravenous injection of the B16-BL6 murine melanoma in C57BL/6N mice. Chirivi, R.G.S. et al., *Int. J. Cancer* 58, 460–464 (1994). Over-expression of TIMP-2, the endogenous tissue inhibitor of MMP-2, markedly reduced melanoma growth in the skin of immunodeficient mice. Montgomery, A. M. P. et al., *Cancer Res.* 54, 5467–5473 (1994).

Accelerated breakdown of the extracellular matrix of articular cartilage is a key feature in the pathology of both rheumatoid arthritis and osteoarthritis. Current evidence suggests that the inappropriate synthesis of MMPs is the key event. Beeley, N. R. A. et al., *Curr. Opin. Ther. Patents,* 4(1), 7–16 (1994). The advent of reliable diagnostic tools have allowed a number of research groups to recognize that stromelysin is a key enzyme in both arthritis and joint trauma. Beeley, N. R. A. et al., Id.; Hasty, K. A. et al., *Arthr. Rheum.* 33, 388–397 (1990). It has also been shown that stromelysin is important for the conversion of procollagenase to active collagenase. Murphy, G. et al., *Biochem. J.* 248, 265–268 (1987).

Furthermore, a range of MMPs can hydrolyse the membrane-bound precursor of the pro-inflammatory cytokine tumor necrosis factor α (TNF-α). Gearing, A. J. H. et al., *Nature* 370, 555–557 (1994). This cleavage yields mature soluble TNF-α and the inhibitors of MMPs can block production of TNF-α both in vitro and in vivo. Gearing, A. J. H. et al., Id.; Mohler, K. M. et al., *Nature* 370, 218–220 (1994); McGeehan, G. M. et al., *Nature* 370, 558–561 (1994). This pharmacological action is a probable contributor to the antiarthritic action of this class of compounds seen in animal models. Beckett, R. P. et al., supra.

Stromelysin has been observed to degrade the $\alpha_1$-proteinase inhibitor which regulates the activity of enzymes such as elastase, excesses of which have been linked to chronic inflammatory disorders such as emphysema and chronic bronchitis. Beeley, N.R.A. et al., supra.; Wahl, R. C. et al., *Annual Reports in Medicinal Chemistry* 25, 177–184 (1990). In addition, a recent study indicates that MMP-12 is required for the development of smoking-induced emphysema in mice. *Science,* 277, 2002 (1997). Inhibition of the appropriate MMP may thus potentiate the inhibitory activity of endogenous inhibitors of this type.

High levels of mRNA corresponding to stromelysin have been observed in atherosclerotic plaques removed from heart transplant patients. Henney, A. M., et al., *Proc. Natl. Acad. Sci.* 88, 8154–8158 (1991). It is submitted that the role of stromelysin in such plaques is to encourage rupture of the connective tissue matrix which encloses the plaque. This rupture is in turn thought to be a key event in the cascade which leads to clot formation of the type seen in coronary thrombosis. MMP inhibition is thus a preventive measure for such thromboses.

Collagenase, stromelysin and gelatinase have been implicated in the destruction of the extracellular matrix of the cornea. This is thought to be an important mechanism of morbidity and visual loss in a number of ulcerative ocular diseases, particularly those following infection or chemical damage. Burns, F. R. et al., *Invest. Opthalmol. and Visual Sci.* 32, 1569–1575 (1989). The MMPs present in the eye during ulceration are derived either endogenously from infiltrating leucocytes or fibroblasts, or exogenously from microbes.

Collagenase and stromelysin activities have been identified in fibroblasts isolated from inflamed gingiva and the levels of enzyme have been correlated with the severity of the gingivitis observed. Beeley, N. R. A. et al., supra.; Overall, C. M. et al., *J. Periodontal Res.* 22, 81–88(1987).

Excessive levels of gelatinase-B in cerebrospinal fluid has been linked with incidence of multiple sclerosis and other neurological disorders. Beeley, N. R. A. et al., supra.; Miyazaki, K. et al., *Nature* 362, 839–841(1993). The enzyme may play a key role in the demyelination of neurones and the breakdown of the blood brain barrier which occurs in such disorders.

SUMMARY OF THE INVENTION

The present invention provides novel 3-substitutedpyrrolidines of formula (1):

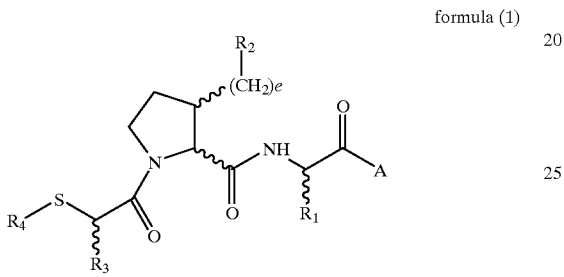

formula (1)

wherein
e is an integer from 0 to 2;
A is selected from the group consisting of —OH and —NRR';
   wherein
   R and R' are independently selected from the group consisting of hydrogen and $C_1$–$C_6$ alkyl or R and R' taken together with the nitrogen atom to which they are attached form a N-morpholino, N-piperidino, N-pyrrolidino, or N-isoindolyl;
$R_1$ is selected from the group consisting of hydrogen, $C_1$–$C_6$ alkyl, —$(CH_2)_a$—$CO_2R_5$, —$(CH_2)_a$—$C(O)NH_2$, —$(CH_2)_4NH_2$, —$(CH_2)_3$—NH—C(NH)$NH_2$, —$(CH_2)_2$—$S(O)_b$—$CH_3$, —$CH_2$—OH, —CH(OH)$CH_3$, —$CH_2$—SH, —$(CH_2)_d$—$Ar_1$, and —$CH_2$—$Ar_2$;
   wherein
   a is 1 or 2;
   b is 0, 1, or 2;
   d is an integer from 0 to 4;
$R_5$ is selected from the group consisting of hydrogen, $C_1$–$C_4$ alkyl, and benzyl;
$Ar_1$ is a radical selected from the group consisting of

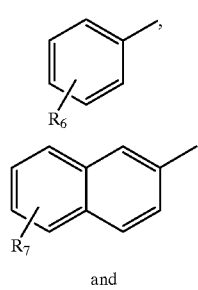

and

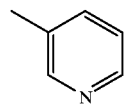

wherein
$R_6$ is from 1 to 2 substituents independently selected from the group consisting of hydrogen, halogen, $C_1$–$C_4$ alkyl, hydroxy, and $C_1$–$C_4$ alkoxy;
$R_7$ is selected from the group consisting of hydrogen, halogen, $C_1$–$C_4$ alkyl, and $C_1$–$C_4$ alkoxy;
$Ar_2$ is a radical selected from the group consisting of

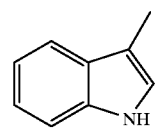

and

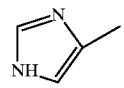

$R_2$ is a radical selected from the group consisting of

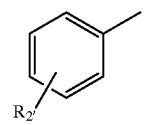

and

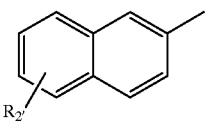

wherein
wherein
$R_{2'}$ is from 1 to 2 substituents selected from the group consisting of hydrogen, halogen, $C_1$–$C_4$ alkyl, and $C_1$–$C_4$ alkoxy;
$R_3$ is selected from the group consisting of $C_1$–$C_6$ alkyl, —$(CH_2)_m$—W, —$(CH_2)_p$—$Ar_3$, —$(CH_2)_k$—$CO_2R_9$, —$(CH_2)_m$—$NR_8$,$SO_2$—$Y_1$, and —$(CH_2)_m$—Z—Q
wherein
m is an integer from 2 to 8;
p is an integer from 0–10;
k is an integer from 1 to 9;
W is phthalimido;
$Ar_3$ is selected from the group consisting of

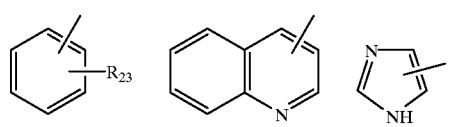

-continued

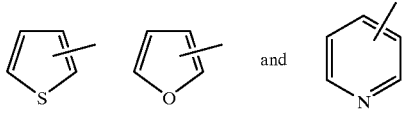

wherein
R$_{23}$ is from 1 to 2 substituents independently selected from the group consisting of hydrogen, halogen, C$_1$–C$_4$ alkyl, and C$_1$–C$_4$ alkoxy;

R$_{8'}$ is hydrogen or C$_1$–C$_6$ alkyl;

R$_9$ is hydrogen or C$_1$–C$_6$ alkyl;

Y$_1$ is selected from the group consisting of hydrogen, —(CH$_2$)$_j$—Ar$_4$, and —N(R$_{24}$)$_2$
wherein
j is 0 or 1;
R$_{24}$ each time selected is independently hydrogen or C$_1$–C$_6$ alkyl or are taken together with the nitrogen to which they are attached to form N-morpholino, N-piperidino, N-pyrrolidino, or N-isoindolyl;

Ar$_4$ is

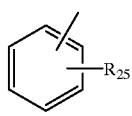

wherein
R$_{25}$ is from 1 to 3 substituents independently selected from the group consisting of hydrogen, halogen, C$_1$–C$_4$ alkyl, and C$_1$–C$_4$ alkoxy;

Z is selected from the group consisting of —O—, —NR$_8$—, —C(O)NR$_8$—, —NR$_8$C(O)—, —NR$_8$C(O)NH—, —NR$_8$C(O)O—, and —OC(O)NH—;
wherein
R$_8$ is hydrogen or C$_1$–C$_6$ alkyl;

Q is selected from the group consisting of hydrogen, —(CH$_2$)$_n$—Y$_2$, and —(CH$_2$)$_x$—Y$_3$;
wherein
n is an integer from 0 to 4;
x is an integer from 2 to 4;
Y$_2$ is selected from the group consisting of hydrogen, —(CH$_2$)$_h$—Ar$_5$ and —(CH$_2$)$_t$—C(O)OR$_{27}$
wherein
Ar$_5$ is selected from the group consisting of

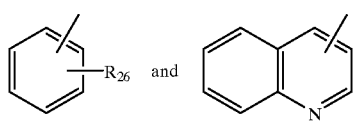

wherein
R$_{26}$ is from 1 to 3 substituents independently selected from the group consisting of hydrogen, halogen, C$_1$–C$_4$ alkyl, and C$_1$–C$_4$ alkoxy;
h is an integer from 0 to 6;
t is an integer from 1 to 6;
R$_{27}$ is hydrogen or C$_1$–C$_6$ alkyl;
Y$_3$ is selected from the group consisting of —N(R$_{28}$)$_2$, N-morpholino, N-piperidino, N-pyrrolidino, and N-isoindolyl;

wherein
R$_{28}$ each time taken is independently selected from the group consisting of hydrogen and C$_1$–C$_6$ alkyl;
R$_4$ is selected from the group consisting of hydrogen, —C(O)R$_{10}$, —C(O)—(CH$_2$)$_q$—K and —S—G
wherein
R$_{10}$ is selected from the group consisting of hydrogen, C$_1$–C$_4$ alkyl, phenyl, and benzyl;
q is 0, 1, or 2;
K is selected from the group consisting of

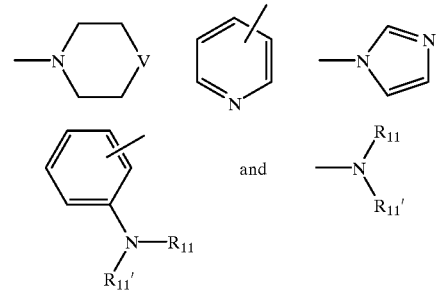

wherein
V is selected from the group consisting of a bond, —CH$_2$—, —O—, —S(O)$_r$—, —NR$_{21}$—, and —NC(O)R$_{22}$—;
wherein
r is 0, 1, or 2;
R$_{21}$ is selected from the group consisting of hydrogen, C$_1$–C$_4$ alkyl, and benzyl;
R$_{22}$ is selected from the group consisting of hydrogen, —CF$_3$, C$_1$–C$_{10}$ alkyl, phenyl, and benzyl;
R$_{11}$ is selected from the group consisting of hydrogen, C$_1$–C$_4$ alkyl, and benzyl;
R$_{11'}$ is selected from the group consisting of hydrogen, C$_1$–C$_4$ alkyl, and benzyl;
G is selected from the group consisting of

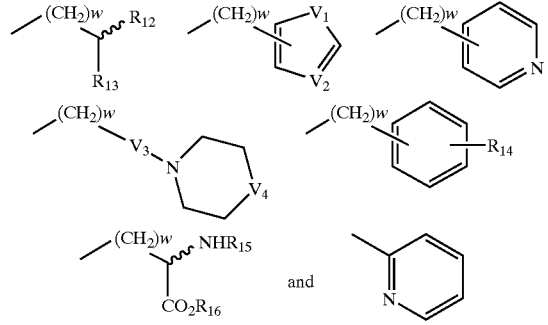

wherein
w is an integer from 1 to 3;
R$_{12}$ is selected from the group consisting of hydrogen, C$_1$–C$_6$ alkyl, —CH$_2$CH$_2$S(O)$_f$CH$_3$, and benzyl;
wherein f is 0, 1, or 2;
R$_{13}$ is selected from the group consisting of hydrogen, hydroxy, amino, C$_1$–C$_6$ alkyl, N-methylamino, N,N-dimethylamino, —CO$_2$R$_{17}$, and —OC(O)R$_{18}$;
wherein
R$_{17}$ is hydrogen, —CH$_2$O—C(O)C(CH$_3$)$_3$, C$_1$–C$_4$ alkyl, benzyl, or diphenylmethyl;
R$_{18}$ is hydrogen, C$_1$–C$_6$ alkyl or phenyl;
R$_{14}$ is 1 or 2 substituents independently selected from the group consisting of hydrogen, C$_1$–C$_4$ alkyl, C$_1$–C$_4$ alkoxy, or halogen;

$V_1$ is selected from the group consisting of —O—, —S—, and —NH—;

$V_2$ is selected from the group consisting of —N— and —CH—;

$V_3$ is selected from the group consisting of a bond and —C(O)—;

$V_4$ is selected from the group consisting of —O—, —S—, —$NR_{19}$—, and —$NC(O)R_{20}$—;

wherein
$R_{19}$ is hydrogen, $C_1$–$C_4$ alkyl, or benzyl;
$R_{20}$ is hydrogen, —$CF_3$, $C_1$–$C_{10}$ alkyl, or benzyl;
$R_{15}$ is selected from the group consisting of hydrogen, $C_1$–$C_6$ alkyl and benzyl;
$R_{16}$ is selected from the group consisting of hydrogen and $C_1$–$C_4$ alkyl; and stereoisomers, pharmaceutically acceptable salt, and hydrate thereof.

The present invention further provides a method of inhibiting matrix metalloproteinases (MMPs) in a patient in need thereof comprising administering to the patient an effective matrix metalloproteinase inhibiting amount of a compound of formula (1). As such the present invention provides a method of treating a neoplastic disease state or cancer; rheumatoid arthritis; osteoarthritis; osteoporosis; cardiovascular disorders, such as atherosclerosis; corneal ulceration; dental diseases, such as gingivitis or periodontal disease; and neurological disorders, such as multiple sclerosis; chronic inflammatory disorders, such as emphysema and especially smoking-induced emphysema.

In addition, the present invention provides a composition comprising an assayable amount of a compound of formula (1) in admixture or otherwise in association with an inert carrier. The present invention also provides a pharmaceutical composition comprising an effective MMP inhibitory amount of a compound of formula (1) in admixture or otherwise in association with one or more pharmaceutically acceptable carriers or excipients.

As is appreciated by one of ordinary skill in the art the compounds of formula (1) exist as stereoisomers. Specifically, it is recognized that they exist as stereoisomers at the point of attachment of the substituents $R_1$, —$(CH_2)_e$—$R_2$, $R_3$, and —$SR_4$, —C(O)NH—$CHR_1$—C(O) A, $R_{12}$, and —$NHR_{15}$. Where indicated the compounds follow either the (+)- and (−)-designation for optical rotation, the (D)- and (L)-designation of relative stereochemistry, or the Cahn-Ingold-Prelog designation of (R)-and (S)- for the stereochemistry of at specific postions in the compounds represented by formula (1) and intermediates thereof. Any reference in this application to one of the compounds of the formula (1) is meant to encompass either specific stereoisomers or a mixture of stereoisomers.

The specific stereoisomers can be prepared by stereospecific synthesis using enantiomerically pure or enantiomerically enriched starting materials which are well known in the art. The specific stereoisomers of amino acid starting materials are commercially available or can be prepared by stereospecific synthesis as is well known in the art or analogously known in the art, such as D. A. Evans, et al. *J. Am. Chem. Soc.,* 112, 4011–4030 (1990); S. Ikegami et al. *Tetrahedron,* 44, 5333–5342 (1988); W. Oppolzer et al. *Tet. Lets.* 30, 6009–6010 (1989); *Synthesis of Optically Active α-Amino-Acids*, R. M. Williams (Pergamon Press, Oxford 1989); M. J. O'Donnell ed.: *α-Amino-Acid Synthesis*, Tetrahedron Symposia in print, No. 33, *Tetrahedron* 44, No. 17 (1988); U. Schöllkopf, *Pure Appl. Chem.* 55, 1799 (1983); U. Hengartner et al. *J. Org. Chem.,* 44, 3748–3752 (1979); M. J. O'Donnell et al. *Tet. Lets.,* 2641–2644 (1978); M. J. O'Donnell et al. *Tet. Lets.* 23, 4255–4258 (1982); M. J. O'Donnell et al. *J. Am. Chem. Soc.,* 110, 8520–8525 (1988).

The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are known in the art and are described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As used in this application:

a) the term "halogen" refers to a fluorine atom, chlorine atom, bromine atom, or iodine atom;

b) the term "$C_1$–$C_6$ alkyl" refers to a branched or straight chained alkyl radical containing from 1 to 6 carbon atoms. Examples include but are not limited to methyl, ethyl, n-propyl, isopropyl, n-butyl, isobutyl, t-butyl, pentyl, hexyl and the like;

c) the term "$C_1$–$C_4$ alkyl" refers to a saturated straight or branched chain alkyl group containing from 1–4 carbon atoms and includes methyl, ethyl, n-propyl, isopropyl, n-butyl, s-butyl, isobutyl, and t-butyl;

d) the term "$C_1$–$C_4$ alkoxy" refers to a straight or branched alkoxy group containing from 1 to 4 carbon atoms. Examples include but are not limited to methoxy, ethoxy, n-propoxy, isopropoxy, n-butoxy, isobutoxy, t-butoxy and the like;

e) the designation "∿∿" refers to a bond for which the stereochemistry is not designated;

f) the designation "—◀" refers to a bond that protrudes forward out of the plane of the page.

g) the designation "⊪⊪⊪" refers to a bond that protrudes backward out of the plane of the page.

h) as used in the examples and preparations, the following terms have the meanings indicated: "g" refers to grams, "mg" refers to milligrams, "µg" refers to micrograms, "mol" refers to moles, "mmol" refers to millimoles, "nmole" refers to nanomoles, "L" refers to liters, "mL" or "ml" refers to milliliters, "µL" refers to microliters, "° C" refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "brine" refers to a saturated aqueous sodium chloride solution, "M" refers to molar, "mM" refers to millimolar, "µM" refers to micromolar, "nM" refers to nanomolar, "HPLC" refers to high performance liquid chromatography, "HRMS" refers to high resolution mass spectrum, "DMF" refers to dimethylformamide, "µCi" refers to microcuries, "i.p." refers to intraperitoneally, "i.v." refers to intravenously, and "DPM" refers to disintegrations per minute;

i) for substituent Z, the designations —$C(O)NR_8$—, —$NR_8C(O)$—, —$NR_8C(O)NH$—, —$NR_8C(O)O$—, and —$OC(O)NH$— refer to the finctionalities represented, respectively, by the following formulae showing the attachment of the group (Q):

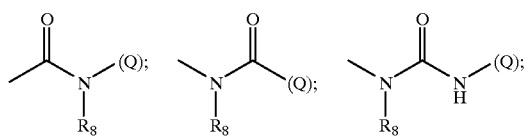

-continued

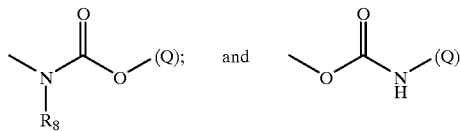

these designations are referred to hereinafter as amido, amide, urea, N-carbamoyl, and O-carbamoyl, respectively; j) the term "pharmaceutically acceptable salts" thereof refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

As with any group of structurally related compounds which possess a particular utility, certain groups and configurations of substituents are preferred for the compounds of formula (1). Preferred embodiments are given below:

The compounds in which $R_1$ is selected from the group consisting of $C_1$–$C_6$ alkyl and —$(CH_2)_d$—$Ar_1$ are preferred;

The compounds in which $R_1$ is —$(CH_2)_d$—$Ar_1$ are more preferred;

The compounds in which $R_1$ is —$(CH_2)_d$—$Ar_1$ in which d is 1 or 2 and $Ar_1$ is phenyl are most preferred;

Compounds in which $R_4$ is selected from the group consisting of hydrogen, —C(O)$R_{10}$ and —SG are preferred;

Compounds in which $R_4$ is selected from the group consisting of —C(O)$R_{10}$ and $R_{10}$ is $C_1$–$C_4$ alkyl more preferred;

Compounds in which A is —OH are preferred; and

Compounds in which A is —NRR' wherein R is hydrogen and R' is methyl are preferred.

Examples of compounds encompassed by the present invention include the following.

It is understood that the examples encompass all of the isomers of the compound and mixtures thereof. This list is meant to be representative only and is not intended to limit the scope of the invention in any way:

(2S,3S)-3-Benzyl-1-((S)-2-mercapto-3-methyl-butanoyl)-pyrrolidine-2-carboxylic acid [(S)-2-(4-hydroxy-phenyl)-1-methylcarbamoyl-ethyl]-amide;

(2S,3R)-3-Benzyl-1-((S)-2-mercapto-3-methyl-butanoyl)-pyrrolidine-2-carboxylic acid [(S)-2-(4-hydroxy-phenyl)-1-methylcarbamoyl-ethyl]-amide;

(2S,3S)-3-Benzyl-1-((S)-2-mercapto-3-methyl-butanoyl)-pyrrolidine-2-carboxylic acid ((S)-1-methylcarbamoyl-2-pyridin-3-yl-ethyl)-amide;

(2S,3R)-3-Benzyl-1-((S)-2-mercapto-3-methyl-butanoyl)-pyrrolidine-2-carboxylic acid ((S)-1-methylcarbamoyl-2-pyridin-3-yl-ethyl)-amide;

(2S,3S)-3-Benzyl-1-((S)-2-mercapto-3-methyl-butanoyl)-pyrrolidine-2-carboxylic acid ((R)-1-methylcarbamoyl-2-pyridin-3-yl-ethyl)-amide;

(2S,3R)-3-Benzyl-1-((S)-2-mercapto-3-methyl-butanoyl)-pyrrolidine-2-carboxylic acid ((R)-1-methylcarbamoyl-2-pyridin-3-yl-ethyl)-amide;

(2S,3S)-3-Benzyl-1-((S)-2-mercapto-3-methyl-butanoyl)-pyrrolidine-2-carboxylic acid ((S)-2,2-dimethyl-1-methylcarbamoyl-propyl)-amide;

(2S,3R)-3-Benzyl-1-((S)-2-mercapto-3-methyl-butanoyl)-pyrrolidine-2-carboxylic acid ((S)-2,2-dimethyl-1-methylcarbamoyl-propyl)-amide;

3-Benzyl-1-(2-mercapto-3-methyl-butanoyl)-pyrrolidine-2-carboxylic acid amide; compound with 2-methyl-pentane;

3-Benzyl-1-(2-mercapto-3-methyl-butanoyl)-pyrrolidine-2-carboxylic acid amide; compound with 2,4-dimethyl-pentanoic acid methylamide;

2-({1-[3-Benzyl-1-(2-mercapto-3-methyl-butanoyl)-pyrrolidin-2-yl]-methanoyl}-amino)-4-methyl-pentanoic acid;

3-Benzyl-1-(2-mercapto-3-methyl-butanoyl)-pyrrolidine-2-carboxylic acid phenethylamide;

3-Benzyl-1-(2-mercapto-3-methyl-butanoyl)-pyrrolidine-2-carboxylic acid (1-methylcarbamoyl-2-phenyl-ethyl)-amide;

2-({1-[3-Benzyl-1-(2-mercapto-3-methyl-butanoyl)-pyrrolidin-2-yl]-methanoyl}-amino)-3-phenyl-propionic acid;

3-Benzyl-1-(2-mercapto-3-methyl-butanoyl)-pyrrolidine-2-carboxylic acid (2-pyridin-3-yl-ethyl)-amide;

2-({1-[3-Benzyl-1-(2-mercapto-3-methyl-butanoyl)-pyrrolidin-2-yl]-methanoyl}-amino)-3-pyridin-3-yl-propionic acid;

3-Benzyl-1-(2-mercapto-3-methyl-butanoyl)-pyrrolidine-2-carboxylic acid isobutylamide;

3-Benzyl-1-(2-mercapto-3-methyl-butanoyl)-pyrrolidine-2-carboxylic acid (2-methyl-1-methylcarbamoyl-propyl)-amide; and 2-({1-[3-Benzyl-1-(2-mercapto-3-methyl-butanoyl)-pyrrolidin-2-yl]-methanoyl}-amino)-3-methyl-butyric acid.

The compounds of formula (1) can be prepared by a variety of procedures readily known to those skilled in the art. Such procedures include, peptide coupling, such as solid phase sequential procedures and solution phase sequential procedures using suitable amino acids and substituted acids and displacement, modification, and functionalization procedures, as required, utilizing suitable protecting groups and deprotection procedures.

As used herein the term "amino acid" refers to naturally occurring amino acids as well as non-naturally occurring amino acids having substituents encompassed by $R_1$ and $R_2$ as described above. The naturally occurring amino acids included are glycine, alanine, valine, leucine, isoleucine, serine, methionine, threonine, phenylalanine, tyrosine, tryptophan, cysteine, histidine, aspartic acid, asparagine, glutamic acid, glutamine, arginine, ornithine, and lysine. Non-naturally occurring amino acids within the term "amino acid," include without limitation, the D-isomers of the naturally occurring amino acids, norleucine, norvaline, alloisoleucine, t-butylglycine, methionine sulfoxide, and methionine sulfone. Other non-naturally occurring amino acids within the term "amino acid," include without limitation phenylalanines, phenylglycines, homophenylalanines, 3-phenylpropylglycines, 4-phenylbutylglycines; each including those substituted by $R_6$ and $R_{6'}$ as described above; and 1-naphthylalanines and 2-naphthylalanines; including those substituted by $R_7$ and $R_{7'}$ as described above.

The compounds of formula (1) can be prepared by utilizing techniques and procedures well known and appreciated by one of ordinary skill in the art. To illustrate, general synthetic schemes for preparing intermediates and the compounds of formula (1) are set forth below. In the reaction schemes below, the reagents and starting materials are readily available to one of ordinary skill in the art and all substituents are as previously defined unless otherwise indicated.

or gives rise after deprotection to $R_1$ as desired in the final compound of formula (1) and A' is —NRR' as desired in the final product of formula (1) or a protected carboxy group which gives rise to —OH as desired in the final product of formula (1). A' may also be an attachment to a suitable resin. Such a protected carboxy or resin is chosen so that it does not interfere with subsequent deprotection, displacement, derivitivization, functionalization, or modification reactions, as are required. The use and removal of carboxy protecting groups is well known and appreciated in the art and described in *Protective Groups in Organic Synthesis*, Theodora W. Greene (Wiley-Interscience, 2nd Edition, 1991). In addition, an appropriate compound of formula (3a) may also be one in which the stereochemistry at the $R_1$ bearing carbon is as desired in the final product of formula (1).

Such coupling reactions are carried out by a variety of procedures readily known to those skilled in the art. Such procedures include, peptide coupling, such as solid phase sequential procedures and solution phase sequential procedures using suitable amino acids and substituted acids Reaction Scheme A

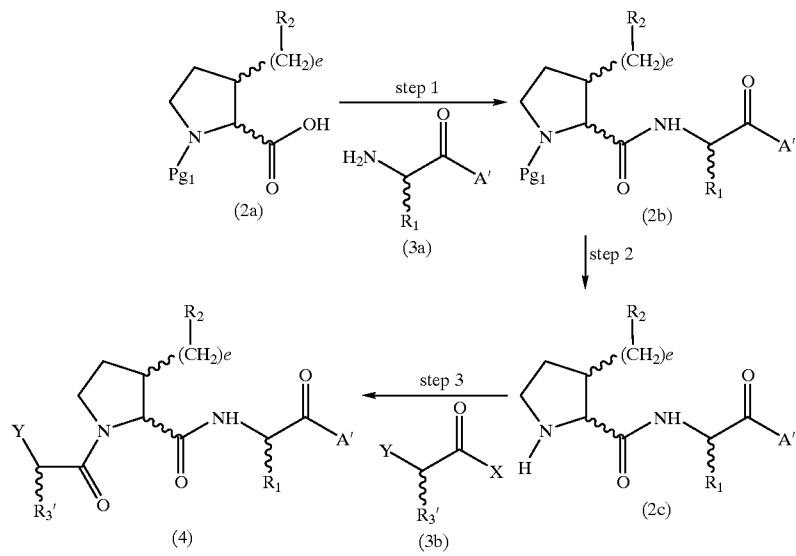

In Scheme A, step 1, an appropriate protected compound of the formula (2a) is coupled with an appropriate compound of formula (3a) to give a compound of formula (2b). An appropriate protected compound of the formula (2a) is one in which $R_2$ is as desired in the final compound of formula (1) or gives rise after deprotection to $R_2$ as desired in the final compound of formula (1), e is as desired in the final product of formula (1), and $Pg_1$ is an amine protecting group. In addition, an appropriate compound of formula (2a) may also be one in which the stereochemistry at the carboxy and —$(CH_2)_e$—$R_2$ bearing carbons is as desired in the final product of formula (1). In Reaction Scheme A the protecting group, $Pg_1$, is one in which the can be removed in the presence of the amide formed in this step. The use and removal of amine protecting groups is well known and appreciated in the art and described in *Protective Groups in Organic Synthesis*, Theodora W. Greene (Wiley-Interscience, 2nd Edition, 1991). In Reaction Scheme A, the use of t-Boc and F-moc for $Pg_1$ is preferred.

An appropriate compound of the formula (3a) is one in which $R_1$ is as desired in the final compound of formula (1)

followed by displacement, modification, and functionalization procedures, as required, utilizing suitable protecting groups and deprotection procedures.

As used herein the term "amino acid" refers to naturally occurring amino acids as well as non-naturally occurring amino acids having substituents encompassed by $R_1$ and —$(CH_2)_e$—$R_2$ as described above. The naturally occurring amino acids included are glycine, alanine, valine, leucine, isoleucine, serine, methionine, threonine, phenylalanine, tyrosine, tryptophan, cysteine, histidine, aspartic acid, asparagine, glutamic acid, glutamine, arginine, omithine, and lysine. Non-naturally occurring amino acids within the term "amino acid," include without limitation, the D-isomers of the naturally occurring amino acids, norleucine, norvaline, alloisoleucine, t-butylglycine, methionine sulfoxide, and methionine sulfone. Other non-naturally occurring amino acids within the term "amino acid," include without limitation phenylalanines substituted by $R_6$ as described above; phenylglycines, homophenylalanines, 3-phenylpropylglycines, 4-phenylbutylglycines; including those substituted by $R_6$ as described above; and 2-naphthylalanines, including those substituted by $R_7$ as described above. The preparation of amino acids bearing —$(CH_2)_e$—$R_2$ are knkown in the art and described herein.

Solid phase sequential procedures can be performed using established methods, including automated methods such as by use of an automated peptide synthesizer. Steward and Young, *Solid Phase Peptide Synthesis* (Freeman 1969) and B. Merrifield, *Peptides: Synthesis, Structures, and Applications* (B. Gutte, Ed., Acedemic Press 1995). In this procedure a protected amino acid bearing $R_1$ or protected $R_1$ is bound to a resin support. The resin support employed can be any suitable resin conventionally employed in the art for the solid phase preparation of poly-peptides, preferably polystyrene which has been crossed away with about 0.5 to about 3 percent divinyl benzene, which has been either in chloromethylated or hydroxymethylated to provide sites for ester formation with the initially introduced protected amino acid. Suitable resins are well known and appreciated in the art, including those described in Rink, *Tet. Let.*, 28, 3787 (1987) and Sieber, *Tet. Let.*, 28, 2107 (1987). Included within the solid phase methods are combinatorial methods which are known in the art. K. S. Lam, Chem. Rev., 97, 411–448 (1997).

In a subsequent step the resin-bound protected amino acid bearing $R_1$ is sequentially amino deprotected and coupled with a protected amino acids bearing —$(CH_2)_e$—$R_2$ to give a resin-bound protected dipeptide. This resin bound protected dipeptide is sequentially amino deprotected and coupled with a protected amino acid bearing $R_3$ or protected $R_3$ to give a protected tripeptide. Alternately, an appropriate protected dipeptide may be coupled by the solution method prior to coupling with the resin-bound amino acid.

Each protected amino acids or amino acid sequence is introduced into the solid phase reactor and about a two-fold to four-fold excess. The coupling is carried out in a suitable medium, for example dimethylformamide, dichloromethane, or mixtures of dimethylformamide and dichloromethane. As is well known and appreciated in the art, wherein complete coupling occurs, the coupling in procedure is repeated before removal of the protecting group, prior to the coupling of the next amino acids in the solid phase reactor.

After the compound of formula (1) or protected compound of formula (1) has been obtained it is removed from the resin under conditions well known in the art which are appropriate for the resin selected.

Compounds of formula (1) obtained by solid phase sequential procedures can be purified by procedures well known and appreciated in the art, such as chromatography, lyophilzation, trituration, salt formation, and crystallization.

The compounds of formula (1) can also be prepared by solution phase sequential procedures well known and appreciated in the art. Accordingly, suitably protected amino acids, substituted acids or dipeptides are coupled by procedures requiring activation of the carbonyl group and coupling reaction with amine function of an appropriate protected amino acid or dipeptide. These procedures are well known appreciated in the art. The selection of an appropriate coupling reagent is within the skill of the art. Particularly suitable coupling reagents include 1-hydroxybenzotriazole (HOBt), 1-hydroxy-7-azabenzotriazole (HOAt), N-((dimethylamino)-1H-1,2,3-triazolo[4,5-b]pyridin-1-ylmethylene)-N-methylmethanaminium hexafluororphosphate N-oxide (HATU), 1-(3-dimethylaminopropyl)-3-ethylcarbodiimide hydrochloride and 1-hydroxy-benzotriazole or N,N-diisopropylcarbodiimide and 1-hydroxy-benzotriazole. Other coupling agents are pyridine benzotriazol-1-yloxytris(dimethylamino)phosphonium hexafluorophosphate complex, carbodiimides (e.g., N,N-dicyclohexylcarbodiimide); cyanamides (e.g., N,N-dibenzylcyanamide); (3b) ketenimines; isoxazolium salts (e.g., N-ethyl-5-phenyl-isoxazolium-3'-sulfonate; monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; alkoxylated acetylene (e.g., ethoxyacetylene); reagents which form a mixed anhydride with the carboxyl moiety of the amino acid (e.g., ethylchloroformate and isobutylchloroformate). Other activating reagents and their use in peptide coupling are described by Kapoor, *J. Pharm. Sci.*, 59, 1–27 (1970).

Such coupling reactions to form amides are carried out in suitable solvents, such as dichloromethane, tetrahydrofuran, diethyl ether, chloroform, and the like, and using suitable bases, such as triethylamine, N-methylmorpholine, N,N-disopropylethylamine, pyridine, and the like, and coupling reagents, as required, and are well known and appreciated in the art. The reactions are generally carried out at −10 C. to the refluxing temperature of the solvent and generally require form 1 hour to 2 days. The product can be isolated and purified by techniques well known in the art, such as extraction, evaporation, trituration, lyophilization, chromatography, and recrystallization.

In Reaction Scheme A, step 2, the amine protecting group, $Pg_1$, of the compound of formula (2b) is selectively removed to give the compound of formula (2c). Such selective amine deprotection reactions are well known and appreciated in the art. The product can be isolated and purified by techniques well known in the art, such as extraction, evaporation, salt formation, trituration, lyophilization, chromatography, and recrystallization.

In Reaction Scheme A, step 3, a compound of formula (2c) coupled with an appropriate acid derivative bearing $R_{3'}$ and Y (compound of formula (3b)) to give a compound of formula (4). Such coupling reactions are well known and appreciated in the art and discussed above. The product can be isolated and purified by techniques well known in the art such as extraction, evaporation, salt formation, trituration, lyophilization, chromatography, and recrystallization.

An appropriate compound of formula (3b) is one in which $R_{3'}$ is $R_3$ as desired in the final product of formula (1) or gives rise after deprotection to $R_3$ as desired in the final product of formula (1) and Y is a protected thio substituent or Y may be a protected hydroxy substituent or bromo which gives rise upon selective deprotection and displacement or displacement and further deprotection and/or elaboration, if required, to —$SR_4$ as desired in the final product of formula (1). Alternately, an appropriate compound of formula (3b) may also be one in which $R_{3'}$ gives rise to $R_{3''}$ which, upon derivatization, gives rise $R_3$ as desired in the final product of formula (1) and Y is a protected thio substituent. In addition, an appropriate compound of formula (3b) may also be one in which the stereochemistry at the $R_{3'}$ and Y bearing carbon is as desired in the final product of formula (1) or gives rise after displacement to the stereochemistry as desired at that carbon in the final product of formula (1). The activating group (A) is one which undergoes an amidation reaction. As is well known in the art an amidation reaction may proceed through an acid, X is —OH; or an acid may be first converted to an acid chloride, X is —Cl; or an activated intermediate; such as an anhydride; a mixed anhydride of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; of an activated ester, such as phenol ester, p-nitrophenol ester, 2,4-dinitrophenol ester, pentafluorophenol ester, pentachlorophenol ester, N-hydroxysuccinimide ester, N-hydroxyphthalimide ester, 1-hydroxy-1H-benztriazole ester, and the like; activated amide, such as imidazole, dimethylpyrazole, triazole, or tetrazole; or an intermediate formed in the presence of coupling agents, such as dicyclohexylcarbodiimide or 1-(3-dimethyaminopropyl)-3-ethylcarbodiimide. Acid chlorides and activated intermediates may be prepared but are not necessarily isolated before the addition of a compound of formula (3b).

The use and selection of appropriate protecting groups is within the ability of those skilled in the art and will depend upon compound of formula (3b) to be protected, the presence of other protected amino acid residues, other protecting groups, and the nature of the particular $R_3$ and/or $R_4$ group(s) ultimately being introduced. Compounds of formula (3b) in which Y is bromo and protected thio are commercially available or can be prepared utilizing materials, techniques, and procedures well known and appreciated by one of ordinary skill in the art or described herein. See PCT Application WO 96/11209, published Apr. 18, 1996. Examples commercially available compounds of formula (3b) in which Y is bromo include 2-bromopropionic acid, 2-bromobutyric acid, 2-bromovaleric acid, 2-bromohexanoic acid, 6-(benzoylamino)-2-bromohexanoic acid, 2-bromoheptanoic acid, 2-bromooctanoic acid, 2-bromo-3-methylbutyric acid, 2-bromoisocaproic acid, 2-bromo-3-(5-imidazoyl)proionic acid, (R)-(+)-2-bromopropionic acid, (S)-(−)-2-bromopropionic acid.

In Reaction Scheme B a final product of formula (1) is prepared from a compound of formula (4) (prepared as described in Reaction Scheme A) in which $R_3'$ is $R_3$ as desired in the final product of formula (1) or gives rise after deprotection to $R_3$ as desired in the final product of formula (1) and Y is a protected thio substituent or hydroxy or bromo.

Reaction Scheme B

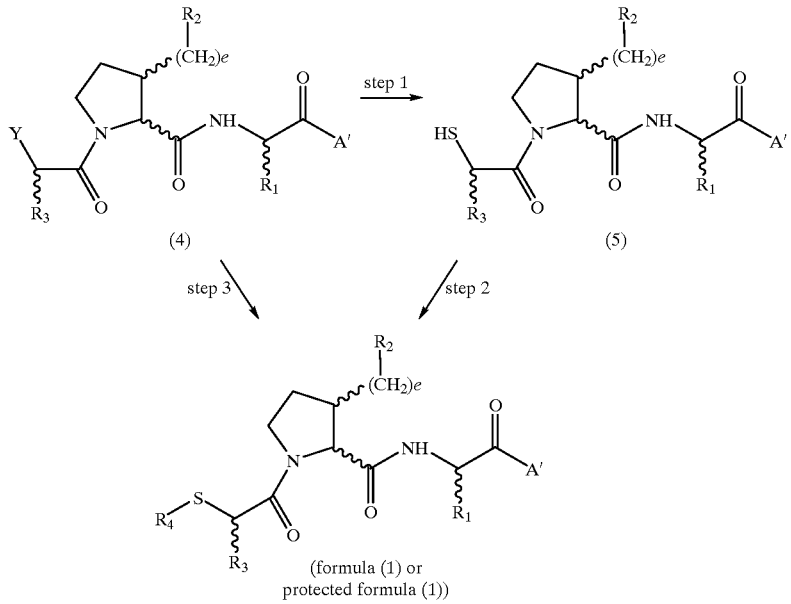

(formula (1) or protected formula (1))

In Reaction Scheme B, step 1, a compound of formula (4) in which Y is protected thio gives rise upon selective deprotection to give a compound of formula (5).

For example, compounds of formula (4) in which Y is a protected thio substituents are selectively deprotected to give a thiol of formula (5). Protected thio substituents include thioesters, such as thioacetyl or thiobenzoyl, thioethers, such as thiobenzyl, thio-4-methoxybenzyl, thiotriphenylmethyl, or thio-t-butyl, or unsymmetrical sulfides, such as dithioethyl or dithio-t-butyl. The use and selective removal of such thio protecting groups is well known and appreciated in the art and described in *Protective Groups in Organic Synthesis*, Theodora W. Greene (Wiley-Interscience, 2nd Edition, 1991).

In Reaction Scheme B, step 2, a compound of formula (5) undergoes modification reaction to give a compound of formula (6). Such modification reactions include, thiol esterification and disulfide formation.

Compounds of formula (6) in which $R_4$ is —C(O)$R_{10}$ or -C(O)—(CH$_2$)$_q$—X group can be synthesized by thiol esterifications according to techniques well known and appreciated by one of ordinary skill in the art, such as those disclosed in U.S. Pat. Nos. 5,424,425, issued Jun. 13, 1995. For example, in a thiol esterification a compound of formula (5) is contacted with about an equimolar amount of an appropriate acid, such as HO—C(O)$R_{10}$ or HO—C(O)—(CH$_2$)$_q$—K in the presence of a suitable coupling agent to give a compound of formula (6) in which $R_4$ is —C(O)$R_{10}$ or —C(O)—(CH$_2$)$_q$—K. The reaction is carried out in the presence of a coupling agent such as 1-hydroxybenzotriazole (HOBt), 1-hydroxy-7-azabenzotriazole (HOAt), 2-fluoro-1-methylpyridinium p-toluenesulfate, 1-(3-dimethylaminopropyl)-3-ethylcarbodiimide hydrochloride, carbonyldiimidazole, 1-ethoxycarbonyl-2-ethoxy-1,2-dihydroquinoline, or diethylcyanophosphonate in a suitable aprotic solvent such as methylene chloride. The reaction is generally carried out at temperature of between −20° C. and the boiling point of the solvent. Generally, the reaction requires 1 to 24 hours. The product can be isolated and purified by techniques well known in the art, such as extraction, evaporation, trituration, lyophilization, chromatography, and recrystallization.

Compounds of formula (6) in which $R_4$ is —S—G group can be synthesized according to techniques well known and appreciated by one of ordinary skill in the art, as disclosed in PCT Application No. WO 95/21839, published Aug. 17, 1995 and U.S. Pat. No. 5,491,143, issued Feb. 13, 1996, and U.S. Pat. No. 5,731,306, issued Mar. 24, 1998, and Roques, B. P. et al., *J. Med. Chem.* 33, 2473–2481 (1992).

For example, in a disulfide formation a compound of formula (5) is contacted with an appropriate compound of formula (7).

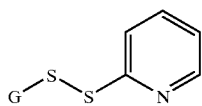

(7)

An appropriate compound of formula (7) is one which gives G as desired in the final product of formula (1) or gives rise upon deprotection to G as is desired in the final product of formula (1). In addition, the compound of formula (7) may have stereochemistry as desired in the final product of formula (1). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of formula (7). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation and can be purified by chromatography and recrystallization.

In Reaction Scheme B, step 3, a compound of formula (4) in which Y is hydroxy or bromo can be displaced by an appropriate thiol, $HSR_4$, to give a compound of formula (1) or a protected compound of formula (1). In Reaction Scheme B, step 3, an appropriate thiol $HSR_4$ is one which gives $R_4$ as desired in the final product of formula (1) or gives rise to $R_4$ as desired in the final product of formula (1).

In Reaction Scheme B, step 3, a compound of formula (4) in which Y is hydroxy (obtained from protected hydroxy compounds of formula (4)) undergoes a displacement reaction with an appropriate thio introducing reagent by the method of Mitsunobu to give a compound of formula (4) in which Y is a protected thio substituent or —$SR_4$ as desired in the final compound of formula (1). For example, a compound of formula (4) in which Y is hydroxy reacts with thioacetic acid or thiobenzoic acid, triphenylphosphine, and diethylazodicarboxylate in a suitable aprotic solvent, such as tetrahydrofuran to give a compound of formula (4) in which Y is thioacetyl or thiobenzoyl. Selective removal of the thioacetic acid or thiobenzoic acid moiety gives the desired compound of formula (5). The product can be isolated and purified by techniques well known in the art, such as extraction, evaporation, trituration, lyophilization, chromatography, and recrystallization.

Also, in Reaction Scheme B, step 3, a compound of formula (4) in which Y is bromo undergoes a displacement reaction with an appropriate thio introducing reagent to give a compound of formula (4) in which Y is protected thio substituent which gives rise upon deprotection and subsequent elaboration, if desired, the —$SR_4$ as desired in the final compound of formula (1). An appropriate thio introducing reagent is also one which introduces a group —$SR_4$ as desired in the final compound of formula (1).

For example, a solution of p-methoxybenzylmercaptan in a suitable organic solvent such as dimethylformamide is degassed and treated with a suitable base such as sodium hydride, sodium hydroxide, or cesium carbonate. After about 1 to 2 hours, a solution of a compound of formula (4) in which Y is bromo is added. The reaction may benefit from the addition of a suitable catalyst, such as tetra-n-butylammonium iodide. The reaction mixture is carried out for 1 to 25 hours at temperatures ranging form 0° C. to about 100° C. Selective removal of the 4-methoxybenzyl moiety gives the desired compound of formula (1). The product can be isolated and purified by techniques well known in the art, such as extraction, evaporation, trituration, lyophilization, chromatography, and recrystallization.

In addition, in Reaction Scheme B, step 3, a compound of formula (4) in which Y is bromo can be displaced by an appropriate thio ester, $Ph_3S$—C(O)—$(CH_2)_q$—X by techniques well known and appreciated in the art, as disclosed in U.S. Pat. No. 5,424,425, issued Jun. 13, 1995.

In Reaction Scheme B, in an optional step, a protected compound of formula (1) is deprotected to give a compound of formula (1). Such deprotection reactions are well known appreciated in the art and may include selective deprotections.

In Reaction Scheme C a final product of formula (1) is prepared from a compound of formula (4) (prepared as described in Reaction Scheme A) in which $R_3$, gives rise to $R_{3''}$ and Y is —$SR_4$ as is desired in the final product of formula (1) or a protected thio substituent gives a compound of formula (1).

Reaction Scheme C

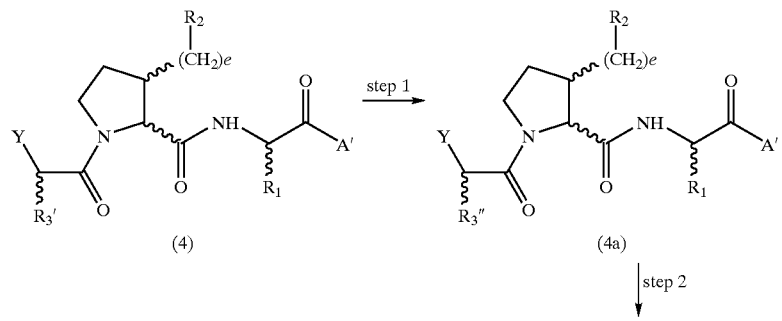

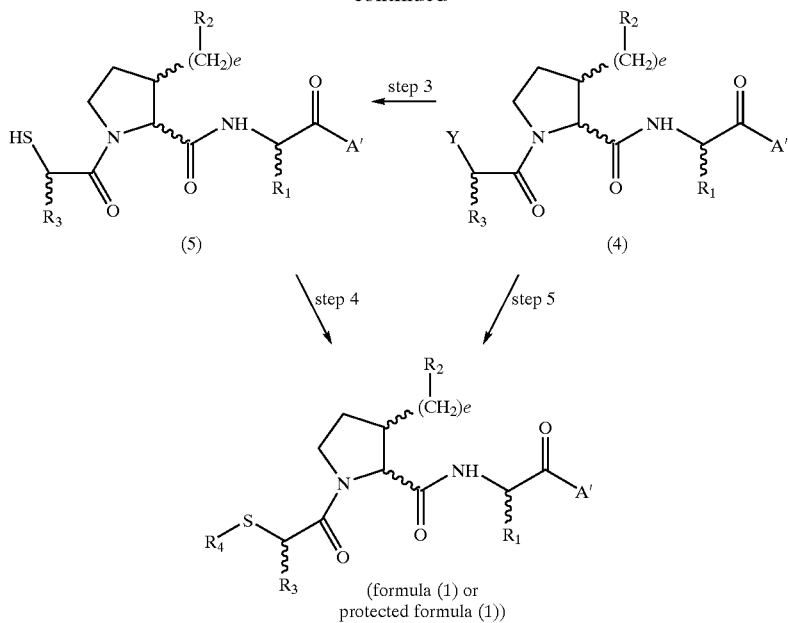

(formula (1) or protected formula (1))

In Reaction Scheme C, step 1, an appropriate compound of formula (4) is deprotected, hydrolyzed, or reduced to give a compound of formula (4a). In Reaction Scheme C, step 1, an appropriate compound of formula (4) is one in which $R_3$ gives rise to a compound of formula (4a) in which $R_{3''}$ undergoes further derivitization (step 2) to give a compound of formula (4) in which $R_3$ is —$(CH_2)_m$—$NR_8$—$SO_2$-$Y_1$ or —$(CH_2)_m$—Z—Q as desired in the final product of formula (1). In Reaction Scheme C, step 1, an appropriate compound of formula (4) is one in which Y is —$SR_4$ as desired in the final compound of formula (1) or Y is protected thio which gives rise upon deprotection or deprotection and further functionalization to give —$SR_4$, as desired, in the final product of formula (1) as described in Reaction Scheme B, step 2, above.

For example, in a deprotection a compound of formula (4) in which $R_{3'}$ is —$(CH_2)_m$—W (W is a phthalimido group) is contacted with a molar excess of hydrazine monohydrate to give a compound of formula (4a) in which $R_{3''}$ is —$(CH_2)_m$-$NHR_8$ in which $R_8$ is hydrogen. The reaction is typically carried out in a protic organic solvent, such as methanol or ethanol. The reaction is generally carried out at room temperature for a period of time ranging from 5–24 hours. The product can be isolated by techniques well known in the art, such as extraction, evaporation, and precipitation and can be purified by chromatography and recrystallization.

Alternately, for example, in a deprotection a compound of formula (4) in which $R_{3'}$ is —$(CH_2)_m$—$NR_8$—t-Boc is contacted with a molar excess of a suitable acid to give a compound of formula (4a) in which $R_{3''}$ is —$(CH_2)_m$—$NHR_8$. The reaction is typically carried out in a organic solvent, such as methanol, ethanol, ethyl acetate, diethyl ether, or dioxane. Suitable acids for this reaction are well known in the art, including hydrochloric acid, hydrobromic acid, trifluoroacetic acid, and methanesulfonic acid. The reaction is generally carried out at room temperature for a period of time ranging from 1–10 hours. The product can be isolated by techniques well known in the art, such as extraction, evaporation, and precipitation and can be purified by chromatography and recrystallization.

For example, in a hydrolysis a compound of formula (4) in which $R_{3'}$ is —$(CH_2)_m$—C(O)$OPg_3$ and $Pg_3$ is methyl or ethyl is contacted with about 1 to 2 molar equivalents of lithium hydroxide, sodium hydroxide, or potassium hydroxide to give a compound of formula (4a) in which $R_{3''}$ is —$(CH_2)_m$—$CO_2H$. The reaction is carried out in a suitable solvent, such as methanol, ethanol methanol/water mixtures, ethanol/water mixtures, or tetrahydrofuran/water mixtures and generally requires 1 to 24 hours. The reaction is carried out at temperatures of from about 0° C. to the refluxing temperature of the solvent. The resulting acid is isolated and purified by techniques well known in the art, such as acidification, extraction, evaporation, and precipitation and can be purified by trituration, precipitation, chromatography, and recrystallization.

For example, in a reduction a compound of formula (4a) in which $R_{3'}$ is —$(CH_2)_{m-1}$—$CO_2Pg_3$ in which $Pg_3$ is methyl or ethyl is contacted with a suitable reducing agent, such as lithium borohydride, diisobutylaluminum hydride, 9-borabicyclo[3.3.1]nonane, preferably lithium borohydride to provide a compound of formula (4a) in which $R_{3''}$ is —$(CH_2)_{m-1}$—$CH_2OH$. The reaction is carried out in a suitable solvent, such as dichloromethane, tetrahydrofuran, or toluene, with tetrahydrofuran being preferred. The reaction is carried out at a temperature of from about −30° C. to about 50° C. and generally requires from 2 to 12 hours. The product can be isolated by quenching, extraction, evaporation, and precipitation and can be purified by trituration, chromatography, and recrystallization.

In Reaction Scheme C, step 2, a compound of formula (4a) undergoes a derivitization reaction to give a compound of formula (5) in which $R_3$ is as desired in the final product of formula (1). Such derivitization reactions include hydrolysis of esters and ester formations as are well known in the art, ether formation, amine alkylation, formation of amides, urea formation, carbamate formation, and formation of sulfonamide. In Reaction Scheme C, step 2, the compound of formula (4a) is one in which Y is a protected thio group, such as thioacetyl, thiobenzoyl, 4-methoxybenzyl thiol or t-butylthiol.

For example, in an ether formation a compound of formula (4a) in which $R_{3''}$ is —$(CH_2)_{m-1}$—$CH_2OH$ is contacted with 1 to 10 molar equivalents of a suitable alkylating agent to give a compound of formula (5) in which $R_3$ is —$(CH_2)_m$—Z—Q in which Z is —O—. A suitable alkylating agent is one which transfers Q or protected Q as desired in the final product of formula (1), such as benzyl bromide, benzyl chloride, substituted benzyl bromide, substituted benzyl chloride, ethyl bromoacetate, t-butyl bromoaceate, ethyl 3-chloropropionate, ethyl 3-bromopropionate, ethyl 5-bromovalerate, ethyl 4-bromobutyrate, 3-chloropropionamide, 2-bromoethylbenzene, substituted 2-bromoethylbenzene, 1-chloro-3-phenylpropane, 1-bromo-4-phenylbutane, and the like, or nitrogen mustards, including 2-dimethylaminoethyl chloride, 2-diethylaminoethyl chloride, and 3-dimethylaminopropyl chloride. The reaction is carried out in a suitable solvent, such as diethyl ether, tetrahydrofuran, dimethylformamide, dimethyl sulfoxide, or acetonitrile and using a suitable base, such as sodium hydride, potassium hydride, potassium t-butoxide, and lithium diisopropylamide. The reaction is generally carried out at temperatures of −70° C. and room temperature and require from about 1–24 hours. The product can be isolated by techniques well known in the art, such as extraction, evaporation, and precipitation and can be purified by chromatography and recrystallization.

Alternately, as appreciated by those skilled in the art, an ether formation can also be carried out by a procedure similar to the one above using a compound of formula (4a) in which $R_{3''}$ is —$(CH_2)_{m-1}$—$CH_2OH$ in which the hydroxy group is first converted to a leaving group, such as chloro, bromo, or mesylate and a suitable alcohol which transfers Q or protected Q as desired in the final product of formula (1), such as benzyl alcohol, substituted benzyl alcohol, phenol, substituted phenol, and the like. The conversion of hydroxy to leaving groups, such as chloro, bromo, and mesylate are well known and appreciated in the art.

For example, in an amine alkylation a compound of formula (4a) in which $R_{3''}$ is —$(CH_2)_m$—$NHR_8$ is contacted with 1 to 10 molar equivalents of a suitable alkylating agent to give a compound of formula (5) in which $R_3$ is —$(CH_2)_m$—Z—Q in which Z is —$NR_8$—. The reaction may be carried out after protection of the amine function of $R_{3''}$ in which $R_8$ is hydrogen by a suitable protecting group, such as benzyl or t-Boc. For an amine alkylation a suitable alkylating agent is one as described above for the ether formation and also includes alkylhalides, such as methyl iodide, methyl bromide, ethyl bromide, propyl bromide, propyl chloride, butyl bromide, butyl chloride, and the like. The reaction is carried out in a suitable solvent, such as methanol, ethanol, dimethylformamide, or pyridine and using a suitable base, such as sodium carbonate, triethylamine, N,N-diisopropylethylamine or pyridine. The reaction is generally carried out at temperatures of room temperature to the refluxing temperature of the solvent and require from about 1–24 hours. The product can be isolated by techniques well known in the art, such as extraction, evaporation, and precipitation and can be purified by chromatography and recrystallization.

Alternately, for example, in an amine alkylation a compound of formula (4a) in which $R_{3''}$ is —$(CH_2)_m$—$NHR_8$ is contacted in a reductive alkylation with a suitable aldehyde to give a compound of formula (5) in which $R_3$ is —$(CH_2)_m$—Z—Q in which Z is —$NR_8$—. A suitable aldehyde is one which transfers Q or protected Q as desired in the final product of formula (1), such as benzaldehyde and substituted benzaldehydes. The reaction is carried out in a suitable solvent, such as methanol, ethanol, tetrahydrofuran, or mixtures of methanol or ethanol and tetrahydrofuran. The reaction may be carried out in the presence of a drying agent, such as sodium sulfate or molecular sieves. The reaction is carried out in the presence of from 1.0 to 6.0 molar equivalents of a suitable reducing agent, such as, sodium borohydride or sodium cyanoborohydride with sodium cyanoborohydride being preferred. It may be advantageous to maintain the pH in the range of about 4 to 6. The reaction is generally carried out at temperatures of from 0° C. to the refluxing temperature of the solvent. Generally, the reactions require 1 to 72 hours. The product can be isolated by techniques well known in the art, such as extraction, evaporation, and precipitation and can be purified by chromatography and recrystallization.

For example, in an amido formation a compound of formula (4a) in which $R_{3''}$ is is —$(CH_2)_m$—$CO_2H$ is contacted with a suitable amine in an amide formation to give a compound of formula (5) in which $R_3$ is —$(CH_2)_m$—Z—Q in which Z is amido. Such amide formation reactions using carboxy activation or suitable coupling agents are well known in the art and described above. A suitable amine, $HNR_8Q$, gives rise to $R_8$ and Q as desired in the final product of formula (1), such as methylamine, ethylamine, propylamine, butylamine, N-methyl benzylamine, benzyl β-alanine, 4-(3-aminopropyl)morpholine, and the like.

For example, in an amide formation a compound of formula (4a) in which $R_{3''}$ is is —$(CH_2)_m$—$NHR_8$ is contacted with a suitable carboxylic acid in an amide formation to give a compound of formula (5) in which $R_3$ is —$(CH_2)_m$—Z—Q in which Z is amide. Such amide formation reactions using carboxy activation or suitable coupling agents are well known in the art and described above. Suitable carboxylic acids, QC(O)—OH, are ones give rise to Q as desired in the final product of formula (1), such as benzoic acid, substituted benzoic acids, phenyl acetic acids, substituted phenylacetic acids, mono-t-butyl malonate, and the like.

For example, in a urea formation a compound of formula (4a) in which $R_{3''}$ is is —$(CH_2)_m$—$NHR_8$ is contacted with an appropriate isocyanate, O=C=N—Q, to give a compound of formula (5) in which $R_3$ is —$(CH_2)_m$—Z—Q in which Z is urea. An appropriate isocyanate is one which gives rise to Q as desired in the final product, such as phenyl isocyanate, substituted phenyl isocyanate, napthyl isocyanate, ethyl isocyanatoacetate, and the like. The reaction is carried out by adding an equivalent of, or a slight molar excess of, an appropriate isocyanate is added to a solution of a compound of formula (4a) in which $R_{3''}$ is —$(CH_2)_m$—$NHR_8$ in a suitable solvent, such as diethyl ether, benzene, or toluene. The reaction is carried out at temperature of from about 0° C to the refluxing temperature of the solvent and require about 1–24 hours. The product can be isolated and purified by techniques well known in the art, such as filtration, extraction, evaporation, trituration, chromatography, and recrystallization.

For example, in an N-carbamoyl formation a compound of formula (4a) in which $R_{3''}$ is —$(CH_2)_m$—$NHR_8$ is contacted with an appropriate chloroformate to give a compound of formula (5) in which $R_3$ is —$(CH_2)_m$—Z—Q in which Z is N-carbamoyl. An appropriate chloroformate is one which gives rise to Q as desired in the final product of formula (1). Examples of chloroformates include benzyl chloroformate, naphthyl chloroformate, phenyl chloroformate, and substituted phenyl chloroformates, such as 4-chlorophenyl chloroformate, 4-methylphenyl chloroformate, 4-bromophenyl chloroformate, 4-fluorophenyl chloroformate, 4-methoxyphenyl chloroformate and the like. The reaction is carried out by adding an equivalent of, or a slight molar excess of, an appropriate chloro formate to a solution of a compound of formula (4a) in which $R_{3''}$ is —$(CH_2)_m$—$NHR_8$ in a suitable solvent, such as toluene, tetrahydrofuran, dimethylformamide, dichloromethane, pyridine, or chloroform. The reaction is carried out in the presence of an excess of a suitable base, such as triethylamine, sodium carbonate, potassium bicarbonate, pyridine or N,N-diisopropylethylamine. The reaction is carried out at a temperature of from −70° C. to the refluxing temperature of the solvent and generally requires from 30 minutes to 24 hours. The product can be isolated and purified by techniques well known in the art, such as extraction, evaporation, chromatography, and recrystallization.

For example, in an 0-carbamoyl formation a compound of formula (4a) in which $R_{3''}$ is —$(CH_2)_{m-1}$—$CH_2OH$ is contacted with an appropriate isocyanate, as defined above for urea formation, to give a compound of formula (5) in which $R_3$ is —$(CH_2)_m$—Z—Q in which Z is O-carbamoyl. The reaction is carried out in a suitable solvent, such as diethyl ether, tetrahydrofuran, dimethylformamide, or acetonitrile. The reaction may be facilitated by the use of catalytic amount of a suitable base, such as sodium hydride, potassium hydride, or potassium t-butoxide. The reaction is generally carried out at temperatures of from −20° C. to room temperature and require from about 1–24 hours. The product can be isolated by techniques well known in the art, such as extraction, evaporation, and precipitation and can be purified by chromatography and recrystallization.

For example, in a sulfonamide formation to prepare a compound in which $R_3$ is —$(CH_2)_m$—$SO_2NR_8$—$Y_1$, a compound of formula (4a) in which $R_{3''}$ is —$(CH_2)_m$—$NHR_8$ is contacted with an appropriate sulfonamide forming reagent. An appropriate sulfonamide forming reagent, such as a sulfonyl chloride, $Y_1S(O)_2Cl$, or sulfonyl anhydride, $Y_1(O)_2S$—O—$S(O)_2$ $Y_1$, is one which gives rise to $Y_1$ as desired in the final product. Examples of appropriate sulfonamide forming reagents are, benzenesulfonyl chloride, 1-napthalenesulfonyl chloride, 2-napthalenesulfonyl chloride, dansyl chloride, N-morpholinylsulfonyl chloride, N-piperidinylsulfonyl chloride, 2,4,5-trichlorobenzenesulfonyl chloride, 2,5-dichlorobenzenesulfonyl chloride, 2,4,6-triisopropylbenzenesulfonyl chloride, 2-mesitylenesulfonyl chloride, 4-bromobenzenesulfonyl chloride, 4-fluorobenzenesulfonyl chloride, 4-chlorobenzenesulfonyl chloride, 4-methoxybenzenesulfonyl chloride, 4-t-butylbenzenesulfonyl chloride, p-toluenesulfonyl chloride, 2,3,4-trichlorobenzenesulfonyl chloride, 2,5-dimethoxybenzenesulfonyl chloride, 4-ethylbenzenesulfonyl chloride, 3,4-dimethoxybenzenesulfonyl chloride, 2,6-dichlorobenzenesulfonyl chloride, 3-bromobenzenesulfonyl chloride, 4-n-butylbenzenesulfonyl chloride, benzenesulfonic anhydride, 4-toluenesulfonic anhydride, and 2-mesitylenesulfonic anhydride. The reaction is carried out in a suitable solvent, such as tetrahydrofliran, dichloromethane, pyridine, or chloroform and in the presence of an excess of a suitable base, such as triethylamine, sodium carbonate, pyridine, or N,N-diisopropylethylamine. The reaction is carried out at a temperature of from −50° C. to the refluxing temperature of the solvent. The reaction generally requires from 30 minutes to 24 hours. The product can be isolated and purified by techniques well known in the art, such as extraction, evaporation, chromatography, and recrystallization.

In Reaction Scheme C, step 3, a compound of formula (5) in which $R_3$ is as desired in the final product of formula (1) undergoes a selective thiol deprotection to give a compound of formula (5). Such selective thiol deprotections using suitable protecting groups are well known and appreciated in the art as discussed in Reaction Scheme B, step 1, above.

In Reaction Scheme C, step 4, a compound of formula (5) undergoes a modification reaction to give a compound of formula (1) or protected compound of formula (1) as described in Reaction Scheme B, step 2, above.

In Reaction Scheme C, step 5, a compound of formula (4) in which Y is protected thio is deprotected to give a compound of formula (1) or to a protected compound of formula (1).

In Reaction Scheme C, in an optional step, a protected compound of formula (1) is deprotected to give a compound of formula (1). Such deprotection reactions are well known appreciated in the art and may include selective deprotections.

Alternate routes for preparing the compounds of formula (3b) in which Y is bromo are presented in Reaction Schemes F.1 and F.2.

Reaction Scheme F.1

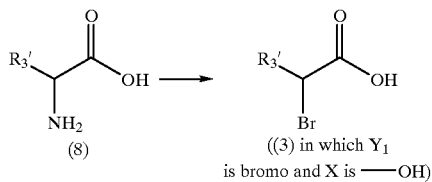

In Reaction Scheme F. 1, an appropriate α-amino carboxylic acid of formula (8) is deaminobrominated to give a compound of formula (3b) in which Y is bromo and X is -OH. An appropriate α-amino carboxylic acid of formula (8), and protected forms thereof, is one which is one in which $R_3$ is $R_3$ as desired in the final product of formula (1) or gives rise after deprotection to $R_3$ as desired in the final product of formula (1) In addition, α-amino carboxylic acid of formula (8) may also be one in which the stereochemistry at the $R_3$ bearing carbon gives rise after displacement to the stereochemistry as desired at that carbon in the final product of formula (1). Such appropriate α-amino carboxylic acid of formula (8), are commercially available or may be readily prepared by techniques and procedures well known and appreciated by one of ordinary skill in the art. For example, L-alanine, D-alanine, L-valine, D-valine, D-norvaline, L-leucine, D-leucine, D-isoleucine, D-tert-leucine, glycine, L-glutamic acid, D-glutamic acid, L-glutamine, D-glutamine, L-lysine, D-lysine, L-ornithine, D-omithine, (D)-(−)-2-aminobutyric acid, D-threonine, D-homoserine, D-allothreonine, D-serine, D-2-aminoadipic acid, D-aspartic acid, D-glutamic acid, D-lysine hydrate, 2,3-diaminopropionic acid monohydrobromide, D-omithine hydrochloride, D,L-2,4-diaminobutyric acid dihydrochloride, L-meta-tyrosine, D-4-hydroxyphenylglycine, D-tyrosine, L-phenylalanine, D-phenylalanine, D,L-2-fluorophenylalanine, beta-methyl-D,L-phenylalanine hydrochloride, D,L-3-fluorophenylalanine, 4-bromo-D,L-phenylalanine, L-phenylalanine, L-phenylglycine, D-phenylglycine, D,L-4-fluorophenylalanine, 4-iodo-D-phenylalanine, D-homophenylalanine, D,L-2-fluorophenylglycine, D,L-4-chlorophenylalanine, and the like, are all commercially available and the methods in D. A. Evans, et al. *J. Am. Chem. Soc.*, 112, 4011–4030 (1990); S. Ikegami et al. *Tetrahedron*, 44, 5333–5342 (1988); W. Oppolzer et al. *Tet. Lets.* 30, 6009–6010 (1989); *Synthesis of Optically Active α-Amino-Acids*, R. M. Williams (Pergamon Press, Oxford 1989); M. J. O'Donnell ed.: *α-Amino-Acid Synthesis*, Tetrahedron Symposia in print, No. 33, *Tetrahedron* 44, No. 17 (1988); U. Schöllkopf, *Pure Appl. Chem.* 55, 1799 (1983); U. Hengartner et al. *J. Org. Chem.*, 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *J. Am. Chem. Soc.*, 110 8520–8525 (1988).

The deaminobromination described in Reaction Scheme F.1 can be performed utilizing conditions described in Compagnone, R. S. and Rapoport, H., *J. Org. Chem.*, 51, 1713–1719 (1986); U.S. Pat. No. 5,322,942, issued Jun. 21, 1994; Overberger, C. G. and Cho, I., *J. Org. Chem.*, 33, 3321–3322 (1968); or Pfister, K. et al., *J. Am. Chem. Soc.*, 71, 1096–1100 (1949).

For example, an α-amino carboxylic acid of formula (8) and a suitable bromide, such as hydrogen bromide or potassium bromide in acidic solution, such as sulfric acid, is treated with sodium nitrite. The reaction temperature is carried out at temperatures of from about −25° C. to about ambient temperature and require about 1 to 5 hours. The product can be isolated and purified by techniques well known in the art, such as acidification, extraction, evaporation, chromatography, and recrystallization to give the compound of formula (3b) in which Y is bromo and X is —OH. The product can be isolated and purified by techniques well known and appreciated in the art, such as acidification, basification, filtration, extraction, evaporation, trituration, chromatography, and recrystallization.

Reaction Scheme F.2

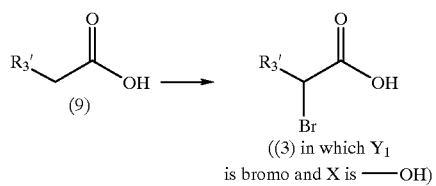

((3) in which $Y_1$ is bromo and X is ——OH)

In Reaction Scheme F.2, an appropriate carboxylic acid of formula (9) is brominated to give compound of formula (3b) in which Y is bromo and X is -OH. An appropriate carboxylic acid of formula (9), and protected forms thereof, is one which is one in which $R_3$ is $R_3$ as desired in the final product of formula (1) or gives rise after deprotection to $R_3$ as desired in the final product of formula (1).

For example, a mixture of a carboxylic acid of formula (9) and dry red phosphorous are treated dropwise with bromine at temperature ranging from about −20° to about 10° C. The reaction mixture is then warmed to room temperature and then heated to about 80° C. for about 2–5 hours. The reaction mixture is then cooled to room temperature, poured into water containing sodium bisulfite, and neutralized using solid sodium carbonate. The aqueous layer is extracted and acidified with a suitable acid, such as concentrated hydrochloric acid. The precipitate is collected by filtration and dried to give the compound of formula (3b) or formula (3b2)in which Y is bromo and X is —OH. The product can be isolated and purified by techniques well known and appreciated in the art, such as acidification, basification, filtration, extraction, evaporation, trituration, chromatography, and recrystallization.

Compounds of formula (8) and (9) in which $R_{3'}$ is a —$(CH_2)_m$—W for use in Reaction Schemes F.1 and F.2 are prepared according to Reaction Scheme G. 1 and G.2.

Reaction Scheme G.1

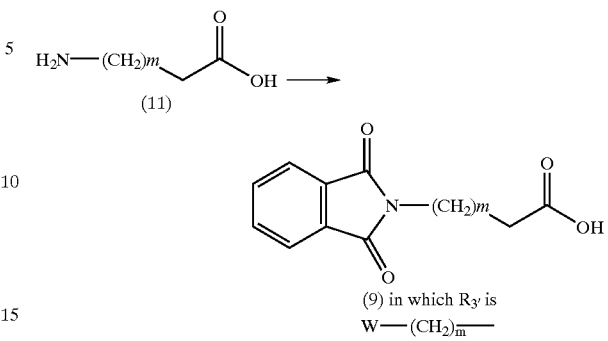

(9) in which $R_{3'}$ is
W——$(CH_2)_{\overline{m}}$——

In Reaction Scheme G.1 an appropriate ω-amino carboxylic acid of formula (11) is converted to an compound of formula (9) in which $R_{3'}$ is W—$(CH_2)_m$—. An appropriate co-amino carboxylic acid of formula (11) is one in which m is as desired in the final product of formula (1) and are readily available in the art. For example, the reaction is carried out in a suitable polar solvent, such as water, ethanol, diethyl ether, tetrahydrofuran, or a water/ethanol solvent mixture using a suitable base, such as sodium carbonate and N-carbethoxyphthalimide. The reaction mixture is typically stirred at about ambient temperature for 1–5 hours. The product can be isolated and purified by techniques well known in the art, such as acidification, extraction, evaporation, chromatography, and recrystallization to give the desired compound of formula (9) in which $R_{3'}$ is W—$(CH_2)_m$—.

Reaction Scheme G.2

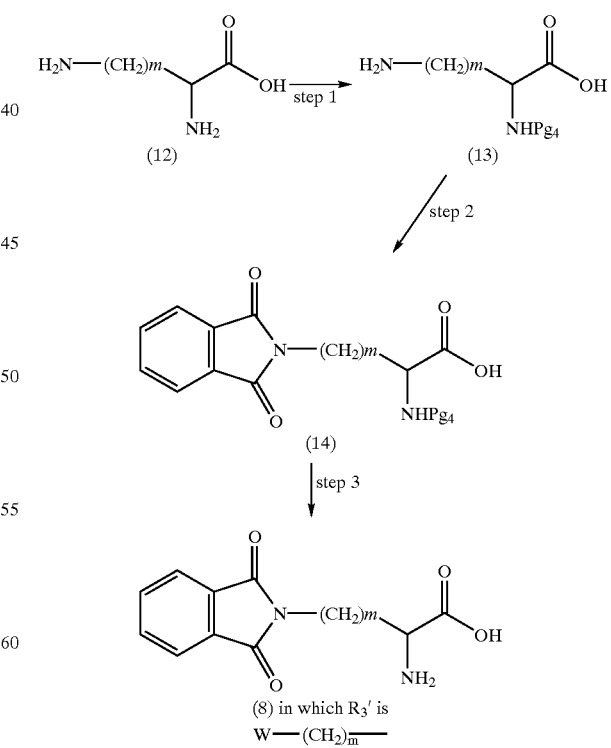

(8) in which $R_3'$ is
W——$(CH_2)_{\overline{m}}$——

Reaction Scheme G.2, step 1, an appropriate α,ω-diamino acid of formula (12) undergoes a selective N-α-protection to give an N-α-protected-ω-diamino acid of formula (13). An appropriate α,ω-diamino acid of formula (12) is one in which m is as desired in the final product of formula (1).

For example, a selective N-a-protection of a suitable α,ω-diamino acid, such as L-lysine (formula 12 in which m is 4), is accomplished by masking the α-amino group by formation of a benzylidene imine. The benzylidene imine is formed by dissolving L-lysine monohydrochloride in lithium hydroxide and cooling the solution to a temperature ranging from about 0° to 10° C. Freshly distilled benzaldehyde is then added and the solution is shaken. N-ω-benzylidene-L-lysine is recovered by filtration and evaporation. The α-amino group of the N-ω-benzylidene-L-lysine then undergoes protection, such as the introduction of a Cbz or t-Boc group, followed by hydrolytic cleavage of the imine in situ to give N-α-benzyloxy-carbonyl-L-lysine. Accordingly, N-ω-benzylidene-L-lysine is added to a mixture of sodium hydroxide and ethanol, cooled to a temperature of from about −5° C. to about −25° C. Then, precooled solutions of benzyloxycarbonyl chloride in a solvent, such as ethanol, is added to the reaction mixture. The temperature is maintained in a range of from about −10° C. to about −25° C. during the course of addition, and may allowed to rise afterwards. The reaction mixture is then acidified using a suitable acid, such as precooled hydrochloric acid, and N-oc-benzyloxycarbonyl-L-lysine, which corresponds to formula (13) where m is 4, is recovered by filtration evaporate and recrystallization.

In Reaction Scheme G.2, step 2, N-α-benzyloxycarbonyl-L-lysine or other compounds of formula (13) is converted to ω-phthalimido-α-benzyloxycarbonyl-L-lysine or other ω-phthalimido-α-aminoprotected carboxylic acid of formula (14) by the method described in Reaction Scheme G. 1, above.

In Reaction Scheme G.2, step 3, the ω-phthalimido-α-aminoprotected carboxylic acid of formula (14) is deprotected to give compound of formula (8) in which $R_{3'}$ is $W-(CH_2)_m-$.

For example, ω-phthalimido-α-benzyloxycarbonyl-L-lysine is contacted with 20 hydrogen in the presence of a hydrogenation catalyst, such as 10% palladium/carbon. The reactants are typically contacted in a suitable solvent mixture such as ethanol, methanol, water, ethanol/water mixtures, or methanol/water mixtures. The reactants are typically shaken under a hydrogen atmosphere of 35–45 psi at room temperature for a period of time ranging from 5–24 hours. The product is typically recovered by filtration and evaporation of the solvent.

A route for preparing the compounds of formula (3b) and formula (3b2) in which $Y_1$ is protected thio is presented in Reaction Scheme H. The reagents and starting materials are readily available to one of ordinary skill in the art. In Reaction Scheme H all substituents, unless otherwise indicated, are as previously defined.

Reaction Scheme H

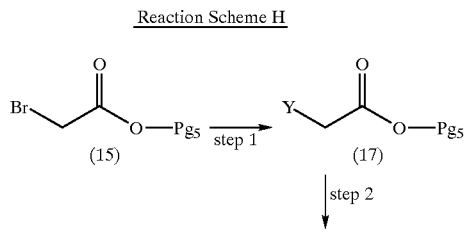

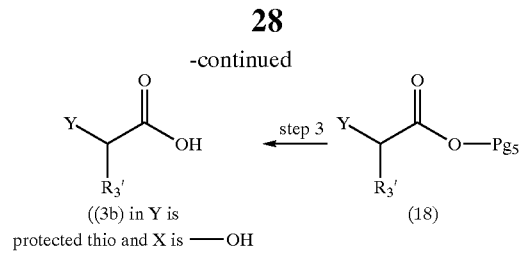

((3b) in Y is protected thio and X is —OH)

In Reaction Scheme H, step 1, a bromoacetate of formula (15) is contacted with an appropriate thiol to give a protected acetic acid ester of formula (17). In a bromoacetate of formula (15) $Pg_5$ is a protecting group, such as methyl, ethyl, t-butyl, and benzyl. An appropriate thiol is one which gives rise to a protected thio group, Y, in the product of formula (3b). In Reaction Scheme H, step 1, the use of 4-methoxybenzylmercaptan is preferred.

For example, a bromoacetate of formula (15) is contacted with an appropriate thiol in a suitable organic solvent, such as dimethylformamide. Advantageously, the solvent is degassed. The reaction is carried out using a suitable base, such as sodium hydroxide, triethylamine, or N,N-diisopropylethylamine. The reaction is carried out at temperatures of from about −50° C. to about ambient temperature and requires about 1 to 72 hours. The protected acetic acid ester of formula (17) can be isolated and purified by methods well known and appreciated in the art, such as extraction, evaporation, chromatography, and distillation, and recrystallization.

In Reaction Scheme H, step 2, the protected acetic acid ester of formula (17) is alkylated with an appropriate akylating agent to give a compound of formula (18). In Reaction Scheme H, step 2, an appropriate alkylating agent is one which transfers $R_{3'}$ which is $R_3$ as desired in the final product of formula (1) or gives rise after deprotection to $R_3$ as desired in the final product of formula (1) or gives rise to $R_{3'}$ as defined in Reaction Scheme C, step 1. Appropriate alkylating agents include alkylhalides, such as methyl iodide, methyl bromide, ethyl bromide, propyl bromide, propyl chloride, butyl bromide, butyl chloride, and the like; benzyl bromide, benzyl chloride, substituted benzyl bromide, substituted benzyl chloride, ethyl bromoacetate, t-butyl bromoaceate, ethyl 3-chloropropionate, ethyl 3-bromopropionate, ethyl 5-bromovalerate, ethyl 4-bromobutyrate, 3-chloropropionamide, 2-bromoethylbenzene, substituted 2-bromoethylbenzene, 1-chloro-3-phenylpropane, 1-bromo-4-phenylbutane, and the like, N-(2-bromoethyl)phthalimide, N-(3-bromopropyl) phthalimide, N-(4-bromobutyl)phthalimide, and the like; 1-bromo-2-phenylethane, 1-bromo-3-phenylpropane, 1-bromo-4-phenylbutane, and the like.

For example, a protected acetic acid ester of formula (17) is alkylated with an appropriate alkylating agent. The reaction is carried out in a suitable solvent, such as diethyl ether, tetrahydrofuran, dimethylformamide, and toluene using a suitable base, such as sodium hydride, potassium hydride, potassium t-butoxide, lithium bis(trimethylsilyl)amide, sodium bis(trimethylsilyl)amide, potassium bis (trimethylsilyl)amide, or lithium diisopropylamide. The reaction is generally carried out at temperatures of about −70° C. to about room temperature and require from about 1–24 hours. The product can be isolated by techniques well known in the art, such as extraction, evaporation, and precipitation and can be purified by chromatography and recrystallization.

In Reaction Scheme H, step 3, the compound of formula (18) the carboxy protecting group $Pg_5$ is selectively removed to give a compound of formula (3b) in which Y is protected thio. Such deprotection of esters to acids in the presence of suitable thio protecting groups are well known and appreciated in the art.

Reaction Scheme I describes the preparation of a specific diastereomer of the compounds of formula (2a).

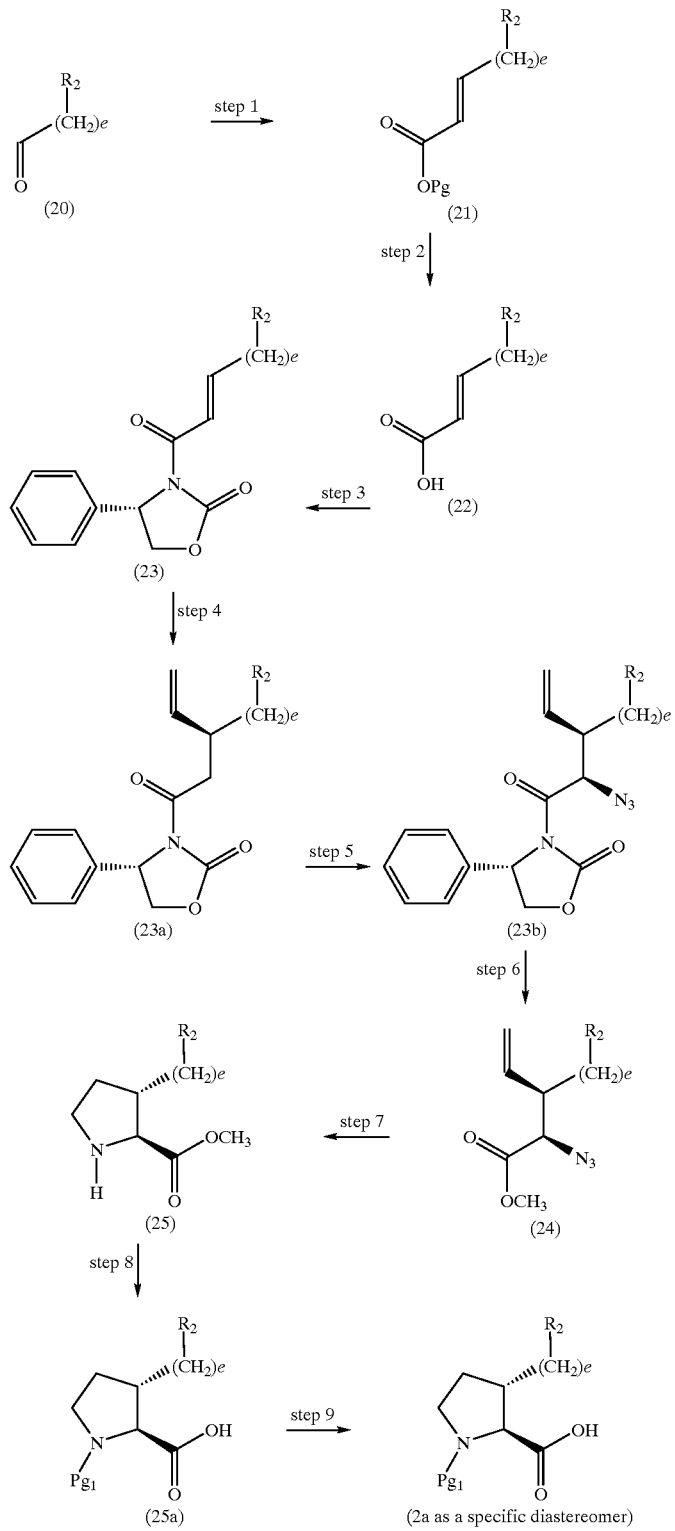

Reaction Scheme I

In Reaction Scheme I, step 1, an appropriate aldehyde of formula (20) is converted to a compound of formula (21) in which Pg is a protecting group. Such conversions can be accomplished by Aldol-type condensation reactions or Wittig-type olefination reactions, each of which are well known in the art. An appropriate aldehyde of formula (20) is one in which e and $R_2$ are as desired in the final product of formula (1). Appropriate aldehydes of formula (20) include, benzaldehyde, substituted benzaldehydes, 1-naphthaldehyde, substitued 1-naphthaldehydes, 2-naphthaldehyde, substitued 2-naphthaldehydes, phenylacetaldehyde, substituted phenylacetaldehydes, hydrocinnamaldehyde, and substituted hydrocinnamaldehyde.

Suitable Aldol-type condensations include the Claisen-Schmidt and Knoevenaglel reactions. *Modem Synthetic Reactions*, H. O. House ($2^{nd}$ Ed. The Benjamin/Cummings Publishing Co. 1972). As is appreciated by one of skill in the art the Claisen-Schmidt reaction using malonic acid, or esters thereof, give compounds of formula (22) upon decarboxylation or hydrolysis and decarboxylation.

Sutiable Wittig-type reacations include the Wittig and Wadswoth-Edmonds reactions. For example, an appropriate aldehyde of formula (20) is reacted with an appropriate reagent, such as (carbethoxymethylene) triphenylphosphorane or dimethyl trimethylsilyloxycarbonylmethyl phosphonate. The reaction is carried out in solvent, such as ethanol, benzene, toluene, or tetrahydrofuran. Typically the reaction is carried out at temperature of from about –20° to reflux and require about 4 to 48 hours. The product can be isolated and purified by techniques well known and appreciated in the art, such as quenching, acidification, filtration, extraction, evaporation, trituration, chromatography, and recrystallization.

Alternately, for example, an appropriate aldehyde of formula (20) is reacted with an appropriate reagent, such as dimethyl trimethylsilyloxycarbonylmethyl phosphonate. The reaction is carried out in solvent, such as benzene, toluene, diethyl ether, or tetrahydrofuran. The reaction is carried out using a suitable base, such as potassium t-butoxide, sodium hydride, lithium diisopropylamide, or sodium or potassium bis(trimethylsilyl)amide. Typically the reaction is carried out at temperature of from about –70° to ambient temperature and require about 1 to 48 hours. The product can be isolated and purified by techniques well known and appreciated in the art, such as quenching, acidification, filtration, extraction, evaporation, trituration, chromatography, and recrystallization.

In Reaction Scheme I, step 2, a compound of formula (21) is hydrolysed to give a compound of formula (22). Such hydrolysis of esters under acidic or basic conditions is well known and appreciated in the art and described in Protective Groups in Organic Synthesis, Theodora W. Greene (Wiley-Interscience, 2nd Edition, 1991).

For example, a compound of formula (21) is reacted with a suitable hydrolyzing agent, such as sodium hydroxide, potassium hydroxide, lithium hydroxide, or sodium carbonate to give an acid. The hydrolysis reaction is carried out in a suitable solvent, such as water, ethanol, methanol, or water/methanol mixtures, water/ethanol mixtures, water/tetrahydrofuran mixtures. The reactions are carried out at temperatures of from 0° C. to the refluxing temperature of the solvent and generally require from 30 minutes to 48 hours. The acid produced in the hydrolysis reaction can be isolated using techniques well known in the art, such as acidification, extraction, and evaporation. The acid may be used after isolation without further purification or may be purified by chromatography, trituration, and recrystallization as is known in the art.

As is appreciated by the skilled person, some of the compounds of formual (22) are readily available and may be available in activated form, such trans-cinnamic acid, substituted trans-cinnamic acids, cinnamoyl chloride, and substituted cinnamoyl chlorides.

In Reaction Scheme I, step 3, a compound of formula (22) is activated and reacted with a lithiated 4-substituted-oxazolidin-5-one to give a compound of formula (23). Suitable 4-substituted-oxazolidin-5-ones include 4-phenyl-2-oxazolidinone, (R)-4-phenyl-2-oxazolidinone, (S)-4-phenyl-2-oxazolidinone, 3,3-dimethyl-4-phenyl-2-oxazolidinone, (R)-3,3-dimethyl-4-phenyl-2-oxazolidinone, and (S)-3,3-dimethyl-4-phenyl-2-oxazolidinone. The use of (R)-4-phenyl-2-oxazolidinone is depicted in Reaction Scheme I.

For example, the compound of formula (22) in a suitable organic solvent, such as tetrahydrofuran diethyl ether, is treated with a suitable tertiary organic amine such as triethylamine or N-methylmorpholine and cooled to –78° C. A suitable acid halide such as trimethylacetyl chloride is added and the mixture is transferred to an ice bath for 0.5 to 1.0 hours, then recooled to -78° C. The resulting slurry is treated with lithiated (R)-4-phenyl-5-oxazolidinone, prepared by adding n-butyllithium to (S)-4-phenyl-2-oxazolidinone in tetrahydrofuran, and allowed to warm gradually to ambient temperature over a period of time ranging from about 10 to 20 hours. The product can be isolated by methods well known and appreciated in the art, such as extraction and evaporation. The product can be purified by methods well known and appreciated in the art, such as flash chromatography.

In Scheme I, step 4, a compound of formula (23) undergoes a 1,4-addition of a vinyl group to give a compound of formula (23a).

For example, a compound of formula (23) and trimethylsilyl chloride in a suitable solvent, such as tetrahydrofuran is added to a prepared solution of copper (I) iodide and N,N,N',N'-tetramethylethylenediamine and vinylmagnesium bromide in tetrhydrofuran. The reaction is carried out at temperatures of from about –78° C. to about 0° C. and requires from about 1 to 12 hours. The product can be isolated and purified by techniques well known and appreciated in the art, such as quenching, acidification, filtration, extraction, evaporation, trituration, chromatography, and recrystallization.

In Scheme I, step 5, a compound of formula (23a) undergoes an azide introduction reaction with a suitable azide transfer agent to give a compound of formula (23b). Such azide introductions are described in the art in *J. Am. Chem. Soc.*, 112, 4011–4030 (1990).

For example, a solution of a suitable amide such as potassium bis(trimethylsilyl)amide in a suitable organic solvent, such as tetrahydrofuran, is cooled to –78° C. and treated with a solution of a compound of formula (32a) in tetrahydrofuran, precooled to –78° C. A solution of a suitable azide transfer agent, such as trisyl azide, prepared by the method described in *J. Org. Chem.*, 38, 11–16 (1973), in a suitable organic solvent, such as tetrahydrofuran, precooled to –78° C. is then added. The solution is stirred, quenched with acetic acid. After a period of time ranging from about 12 to 48 hours, the product is isolated by methods well known and appreciated in the art, such as extraction and evaporation. The product can be purified by methods well known in the art, such as flash chromatography.

In Reaction Scheme I, step 6, a compound of formla (23b) is hydrolyzed and esterified to give a compound of formula (24).

For example, a compound of formula (23b) is reacted with a suitable hydrolyzing agent, such as lithium hydroxide and hydrogen peroxide. The hydrolysis reaction is carried out in a suitable solvent, such as water/tetrahydrofuran mixtures. The reactions are carried out at temperatures of from 0° C. to the refluxing temperature of the solvent and generally require from 30 minutes to 48 hours. The acid produced in the hydrolysis reaction can be isolated using techniques well known in the art, such as quenching of peroxides, acidification, extraction, and evaporation. The acid may be used after isolation without further purification or may be purified by chromatography, trituration, and recrystallization as is known in the art. The acid is then esterified to give a compound of formula (24). For example, to give the methyl ester depicted in Reaction Scheme 1, the acid is contacted with a ester forming reagent, such as (trimethylsilyl) diazomethane. This reaction is carried out in a suitable solvent, such as methanol or methanol/tetrahydrofuran mixtures. The reactions are carried out at temperatures of from 0° C. to the refluxing temperature of the solvent and generally require from 12 to 48 hours. The product can be isolated and purified techniques well known in the art, such as acidification, extraction, evaporation, chromatography, trituration, and recrystallization. Alternately, for example, to give the methyl ester depicted in Reaction Scheme I, the acid is contacted with methanol under acidic conditions. The reactions are carried out at temperatures of from 0° C. to the refluxing temperature of methanol and generally require from 1 to 48 hours. The product can be isolated and purified techniques well known in the art, such as acidification, extraction, evaporation, chromatography, trituration, and recrystallization.

In Reaction Scheme I, step 7, a compound of formula (24) is reduced and cyclized to give a compound of formula (25).

For example, a compound of formula (24) is contacted with a suitable reducing agent, such as dicyclohexylborane. The reaction is carried out in a suitable solvent, such as tetrahydrofuran. The reactions are carried out at temperatures of from −20° C. to ambient temperature and generally require from about 1 to 48 hours. The product can be isolated and purified by techniques well known in the art, such as quenching, extraction, evaporation, chromatography, trituration, and recrystallization.

In Reaction Scheme I, step 8, a compound of formula (25) is protected to give a compound of formula (2a). The use of amine protecting groups is well known and appreciated in the art and described in *Protective Groups in Organic Synthesis*, Theodora W. Greene (Wiley-Interscience, 2nd Edition, 1991).

The following examples present typical syntheses as described in the Reaction Schemes above. These examples and preparations are understood to be illustrative only and are not intended to limit the scope of the invention in any way.

PREPARATION 1
Synthesis of 2-bromo-6-phthalimidohexanoic Acid
6-Phthalimidohexanoic acid (Reaction Scheme G.1)
Combine 6-aminohexanoic acid (6-aminocaproic acid) (8.0 g, 60 mmol) and water (100 mL). Add sodium carbonate (6.84 g, 64 mmol) and N-carbethoxyphthalimide (14.0 g, 64 mmol). After 1.5 hours, extract the reaction mixture with ethyl acetate (100 mL). Cool the aqueous layer in an ice bath and acidify using concentrated hydrochloric acid to give a solid. Collect the solid by filtration, rinse with water, and dry to give 6-phthalimidohexanoic acid (12.7 g, 80% yield).
2-Bromo-6-phthalimidohexanoic Acid (Reaction Scheme F.2)
Combine 6-phthalimidohexanoic acid (12.7 g, 48 mmol) and dry red phosphorous (1.95 g, 63 mmol). Cool in an ice bath and add bromine (12.7 mL, 246 mmol) dropwise. Warm to room temperature and then heat to 80° C. After 3 hours, cool the reaction mixture to ambient temperature, pour into water (300 mL) containing sodium bisulfite, and neutralize using solid sodium bicarbonate and extract with diethyl ether (about 150 mL). Acidify the aqueous layer with concentrated hydrochloric acid to give a solid. Collect the solid by filtration and dry to give the title compound (15 g, 91.5% yield, 73.2% for both steps).

PREPARATION 2
Synthesis of (R)-2-bromo-6-phthalimidohexanoic Acid
(R)-2-N-Carbobenzyloxy-6-phthalamidohexanoic Acid (Reaction Scheme G.2, Step 2)
Combine (R)-2-N-carbobenzyloxy-6-aminohexanoic acid ((R)-Nα-Cbz-lysine) (14.0 g, 50 mmol) and water (500 mL). Add sodium carbonate (5.65 g, 53 mmol) and N-carbethoxyphthalimide (13.15 g, 60 mmol). After 1.5 hours, acidify using concentrated hydrochloric acid to give a solid. Collect the solid by filtration, rinse with water, and dry to give (R)-2-N-carbobenzyloxy-6-phthalamidohexanoic acid.
(R)-2-Amino-6-phthalamidohexanoic Acid Hydrochloric Acid Salt (Reaction Scheme G.2, Step 3)
Combine (R)-2-N-carbobenzyloxy-6-phthalamidohexanoic acid obtained above, methanol (200 mL), 10% palladium-on-carbon (1 g) and treat with hydrogen at atmospheric pressure. After 18 hours, filter, add to the filtrate a solution of hydrochloric acid in methanol (50 mL, 1 M, 50 mmol), and evaporate in vacuo to give (R)-2-amino-6-phthalamidohexanoic acid hydrochloric acid salt.
(R)-2-bromo-6-phthalimidohexanoic Acid (Reaction Scheme F.2)
Combine (R)-2-amino-6-phthalamidohexanoic acid hydrochloric acid salt (12.5 g, 40 mmol) and a 2.5 M aqueous sulfuric acid solution (40 mL). Cool in a salt-ice bath. Add 49% aqueous hydrobromic acid solution (13.2 g). Add dropwise over about 20 minutes, an aqueous solution of sodium nitrite (2.8g, 40 mmol, in 20 mL of water). After 3 hours, warm to ambient temperature. After 18 hours, collect the resultant solid by filtration, rinse with water and dry in vacuo to give a residue. Chromatograph the residue on silica gel eluting with 1/1 ethyl acetate/dichloromethane containing 5% acetic acid to give the title compound.

PREPARATION 3
Synthesis of 1-Fmoc-trans-3-((R)-(naphth-2-yl)-2(S)-carboxypyrrolidine
Ethyl trans-3-(naphth-2-yl)-propenoate (Scheme I, Step 1) Combine 2-naphthaldehyde (7.8 g, 50 mmol) and (carbethoxymethylene) triphenylphosphorane (18.3 g, 52.5 mmol) in 50 mL ethanol (50 mL). After 18 hours, the reaction mixture was diluted with diethyl ether (500 mL)

and washed with aqueous 1 M phosphoric acid solution (2×100 mL), saturated sodium bicarbonate (100 mL), water (100 mL), and then brine (100 mL). Dry the organic layer over MgSO$_4$, filter, and concentrate in vacuo to give a residue. Chromatograph the residue on silica gel eluting with 9:1, hexane:ethyl acetate to give ethyl trans-3-(naphth-2-yl)-propenoate as an 85: 15 mixture of geometric isomers (favoring trans by NMR). Recrystallize from hexane/ethyl acetate to give ethyl trans-3-(naphth-2-yl)-propenoate as a 97:3 mixture of isomers (favoring trans by NMR). Concentrate the mother liquor and recrystallize to recover an additional 2.9 g. (total yield 65%). NMR (CDCl$_3$) δ 7.93 (s, 1H); 7.88–7.83 (c, 4H); 7.67 (dd, 1H, J=1.6, 8.6 Hz); 7.53–7.50 (c, 2H); 6.55 (d, 1H, J=16.0 Hz); 4.30 (q, 2H, J=7.1 Hz); 1.42 (t, 3H, J=7.1 Hz).

Trans-3-(naphth-3-yl)-propenoic Acid (Scheme I, Step 2)

Combine ethyl trans-3-(naphth-2-yl)-propenoate (4.24 g, 18.8 mmol) and tetrahydrofuran (75 mL). Add lithium hydroxide hydrate (2.36 g, 56.3 mmol) in water (19 mL). After 18 hours, acidified to a pH of about 2 with aqueous 12 M hydrochloric acid solution to give a precipitate. Extract with ethyl acetate (3×150 mL). Dry the combined extracts over MgSO$_4$, filter, and concentrated in vacuo to give trans-3-(naphth-2-yl)-propenoic acid as a white solid (3.66 g, 98% yield). NMR (CDCl$_3$) δ 7.97 (d, 1H, J=15.7 Hz); 7.90 (d, 1H, J=15.3 Hz); 7.90–7.83 (c, 3H); 7.70 (dd, 1H, J=1.6, 8.6 Hz); 7.57–7.50 (c, 2H); 6.58 (d, 1H, J=16.0 Hz).

Trans-(4S)-3-(3'-(2"-naphthyl)-propenoyl)-4-phenyl-2-oxazolidinone (Scheme I, Step 3)

Combine trans-3-(naphth-2-yl)-propenoic acid (3.66 g, 18.5 mmol) and triethylamine (1.87 g, 2.56 mL, 18.5 mmol) in tetrahydrofuran (74 mL). Cool to −78° C. Add pivaloyl chloride (2.35 g, 2.40 mL, 19.4 mmol). After 10 minutes, warm in an ice-bath. After 10 minutes, cool to −78° C. Prepare 1-lithio-4-phenyl-2-oxazolidinone in a separate flask by the addition of n-butyl lithium (1.6 M in hexane, 11.6 mL, 18.5 mmol) to 4-phenyl-2-oxazolidinone (3.31 g, 20.3 mmol) in anhydrous tetrahydrofuran (74 mL) at −78° C. After 1.5 hours, add the mixed anhydride prepared above via cannula and place the reaction mixture in an ice-bath. After 1 hour, warm to ambient temperature. After 18 hours, quench with a saturated aqueous ammonium chloride solution (50 mL) and evaprorate to remove most of the tetetrahydrofuran. Extract with dichloromethane (3×75 mL), combine the organic layers, extract an aqueous 1 M sodium hydroxide solution (2×50 mL), dry over MgSO$_4$, filter, and concentrate in vacuo to give a residue. Recrystallize the residue from ethyl acetate/hexane to give trans-(4S)-3-(3'-(2"-naphthyl)-propenoyl)-4-phenyl-2-oxazolidinone as a white solid (61 %). NMR (CDCl$_3$) δ 8.05 (d, 1H, J=15.7 Hz); 7.94 (d, 1H, J=15.4 Hz); 7.87–7.81 (c, 3H); 7.76 (dd, 1H, J=1.5, 8.6 Hz); 7.53–7.47 (c, 2H); 7.41–7.34 (c, 5H); 5.58 (dd, 1H, J=8.7, 3.9 Hz); 4.76 (t, 1H, J=8.7 Hz); 4.33 (dd, 1H, J=8.8, 3.9 Hz).

(3'R,4S)-3-(3'-(2"-Naphthyl)-4'-pentenoyl)-4-phenyl-2-oxazolidinone (Scheme I, Step 4)

To a solution of CuI (3.96 g, 20.9 mol) and N,N,N',N'-tetramethylethylenediamine (2.66 g, 3.46 mL, 22.9 mmol) in anhydrous tetrahydrofuran (92 mL) at −78° C., add vinylmagnesium bromide (1.0 M in tetrahydrofuran, 20.9 mL, 20.9 mmol). Stir the mixture for 15 minutes. In a separate flask, add trimethylsilyl chloride (5.69 g, 6.64 mL, 52.2 mmol) to a solution of unsaturated imide 3 (3.87 g, 11.3 mmol) in anhydrous tetrahydrofuran (42 mL). Owing to insolubility of the imide, remove the septum of the flask containing the cuprate reagent and add the slurried imide in one portion rinsing quickly with a small amount of tetrahydrofuran. Raise the bath temperature to −30° C. and continue stirring for 1 h. Pour the reaction mixture into 250 mL of a 3:2 mixture of saturated ammonium chloride:concentrated NH$_4$OH. Separate the layers and extract the aqueous layer with ethyl acetate (3×200 mL). Wash the combined organic layers sequentially with saturated ammonium chloride (1×100 mL) and water (1×100 mL). Dry the organic layer over MgSO$_4$, and concentrate under reduced pressure. Purify the residue by passaging through a plug of SiO$_2$ and eluting with 4:1 hexane:ethyl acetate. Concentrate the eluant in vacuo to recover a white solid (3.64 g, 9.81 mmol, 87% yield). NMR (CDCl$_3$) δ 7.87–7.82 (c, 3H); 7.72 (s, 1H); 7.54–7.27 (c, 8H); 6.11 (ddd, 1H, J=6.7, 10.4, 17.0 Hz); 5.34 (dd, 1H, J=8.6, 3.5 Hz); 5.10 (d, 1H, J=8.2 Hz); 5.08 (d, 1H, J=17.2 Hz); 4.56 (t, 1H, J=8.8 Hz); 4.26 (dd, 1H, J=8.8, 3.5 Hz); 4.16 (ddd, 1H, J=8.1, 7.0, 6.9 Hz); 3.68 (dd, 1H, J=8.4, 16.5 Hz); 3.50 (dd, 1H, J=6.5, 16.5 Hz).

(2'S,3'R,4S)-3-(2'-Azido-3'-(2"-naphthyl)-4'-pentenoyl)-4-phenyl-2-oxazolidinone (Scheme I, Step 5)

Add potassium hexamethyldisilazide (0.5 M in toluene, 25.5 mL, 12.8 mmol) in one portion to anhydrous tetrahydrofuran (34 mL) at −78° C. Slurry imide 4 (3.64 g, 9.81 mmol) in tetrahydrofuran (34 mL) and add via cannula, rinsing with tetrahydrofuran (2×11 mL) to complete the transfer. After 30 min, dissolve trisylazide (4.40 g, 14.2 mmol) in tetrahydrofuran (34 mL), cool to −78° C., and add via cannula. Thirty minutes later, add acetic acid (1.41 g, 1.34 mL, 23.4 mmol) to quench the reaction. Stir the mixture at room temperature overnight. Partition the mixture between dichloromethane (300 mL) and dilute brine (150 mL). Separate the layers and extract the aqueous phase with dichloromethane (3×150 mL). Dry the combined organic layers over MgSO$_4$, and concentrate under reduced pressure. Purify the residue by flash chromatography to recover the product (3.41 g, 8.28 mmol, 84 % yield). Proton NMR indicates that a byproduct derived from trisylazide was also present. NMR (CDCl$_3$) δ 7.85–7.82 (c, 3H); 7.72 (s, 1H); 7.53–7.47 (c, 2H); 7.42 (dd, 1H, J=1.7, 8.5 Hz); 7.37–7.31 (c, 3H); 7.18–7.15 (c, 2H); 6.28 (ddd, 1H, J=8.2, 10.2, 17.1 Hz); 5.63 (d, 1H, J=10.2 Hz); 5.37 (d, 1H, J=17.0 Hz); 5.34 (d, 1H, J=10.2 Hz); 4.83 (dd, 1H, J=3.0, 8.3 Hz); 4.14 (t, 1H, J=7.2 Hz); 4.07 (dd, 1H, J=9.3, 17.9 Hz); 3.94 (dd, 1H, J=3.0, 5.8 Hz); 3.68 (t, 1H, J=8.6 Hz).

Notes: Trisylazide is not commercially available. Sulfonyl azides can be prepared according to J. Org. Chem. 1973, 38, 11–16. The azide transfer can be difficult. See J. Am. Chem. Soc. 1990, 112, 4011–4030 for a full discussion. After the addition of the trisylazide, an intermediate that is more polar than starting material is rapidly formed. After addition of acetic acid, the polar intermediate slowly disappears and the product azidoimide spot begins to form. It is only slightly less polar than the starting imide. A decomposition product of trisylazide nearly coelutes with the product. Timing of this reaction is critical as the yield erodes with increasing time between addition of the trisylazide and the acetic acid.

Methyl (2S,3R)-2-azido-3-(naphth-2-yl)-4-pentenoate (Scheme I, Step 6)

To a solution of imide 5 (3.41 g, 8.28 mmol) in tetrahydrofuran (62 mL) was add water (21 mL), 35% $H_2O_2$ (2.7 mL), and LiOH—$H_2O$ (695 mg, 16.6 mmol). After 2 hours, add sodium sulfite (4.17 g, 33.1 mmol) as a solution in water (41 mL). Stir the mixture for 15 minutes and remove the tetrahydrofuran under reduced pressure. Acidify the aqueous solution with hydrochloric acid and extract with ethyl acetate (2×150 mL). Dry the combined extracts over $MgSO_4$, and concentrate under reduced pressure. Pass the residue through a $SiO_2$ plug column eluting with 1:1 hexane:ethyl acetate to recover, after concentration, a white solid that is presumably a mixture of the carboxylic acid and chiral auxiliary. Recrystallization from hexane/ethyl acetate yields the chiral auxiliary as needles. Concentrate the mother liquor and carry on to the esterification step.

Dissolve the residue containing the crude carboxylic acid in anhydrous MeOH (46 mL) and cool to 0° C. Add thionyl chloride (1.18 g, 0.725 mL, 9.94 niol) and, after 10 minutes, heat the mixture at reflux for 2 hours. Add water (1.0 mL) to the mixture, stir for 10 minutes, and concentrate the contents of the flask under reduced pressure. Partition the residue between ethyl acetate (150 mL) and brine (100 mL). Separate the layers and dry the organic layer over $MgSO_4$, and concentrate under reduced pressure. Purify the residue by flash chromatography (19:1 hexane:ethyl acetate) to recover the methyl ester (1.54 g, 5.48 mmol, 66% yield). NMR ($CDCl_3$) δ 7.84–7.80 (c, 3H); 7.71 (s, 1H); 7.50–7.46 (c, 2H); 7.39 (dd, 1H, J=1.8, 8.5 Hz); 6.23 (ddd, 1H, J=8.3, 10.9, 17.6 Hz); 5.30 (d, 1H, J=9.9 Hz); 5.28 (d, 1H, J=17.7 Hz); 4.22 (d, 1H, J=7.5 Hz); 4.06 (t, 1H, J=7.9 Hz).

Notes: The intermediate carboxylic acid and chiral auxiliary tend to coelute by flash chromatography and the indicated recrystallization only removed a layer of the auxiliary. The auxiliary was thus present for the esterification step without complication. However under these conditions it has been observed that the auxiliary can ring open and subsequently decarboxylate leaving a primary amine which can attack the ester. If the esterification is run with the auxiliary present, the reaction should be monitored carefully.

Trans-3-(naphth-2-yl)-L-proline methyl Ester (Scheme I, Step 7)

Dilute borane-methyl sulfide complex (2.0 M in tetrahydrofuran, 6.57 mL, 13.1 mmol) with anhydrous tetrahydrofuran (26 mL) and cool to 0° C. Add cyclohexene (2.16 g, 2.66 mL, 26.3 mmol) cautiously via syringe. After 30 minutes a white precipitate forms. Continue stirring for three hours. Concentrate the contents of the flask in vacuo. Note: Care should be taken to minimize air exposure as dicyclohexyl borane is extremely moisture sensitive. Slurry the reagent in dichloromethane (36 mL) and cool to 0° C. Dissolve vinyl azide 6 (1.23 g, 4.38 mmol) in dichloromethane (9 mL) and add via cannula. The reaction mixture becomes pale yellow and gas evolution is evident. Warm the mixture to room temperature overnight. Add methanol (26 mL) and stir for an additional 15 minutes. Concentrate the mixture under reduced pressure. Take the residue up in diethyl ether (25 mL) and extract with 0.1 M hydrochloric acid (5×25 mL). Basify the aqueous extracts with saturated sodium bicarbonate and extract with dichloromethane (3×100 mL). Dry the organic extracts over $MgSO_4$, and concentrate in vacuo to recover the cyclized product along with some dicyclohexyl borane derived contaminants (974 mg, 3.82 mmol, 87% yield of crude material). NMR ($CDCl_3$) δ7.84–7.78 (c, 3H); 7.71 (s, 1H); 7.49–7.41 (c, 3H); 3.91 (d, 1H, J=6.9 Hz); 3.69 (s, 3H); 3.63 (m, 1H); 3.48 (dd, 1H, J=8.2, 15.4 Hz); 3.27 (d, 1H, J=7.8 Hz); 3.25 (d, 1H, J=7.8 Hz); 2.33 (m, 1H), 2.09 (m, 1H).

Note: The cyclization can be capricious. The best results are obtained when fresh bottles of borane were employed. A suggestion is to make the dicylcohexylborane reagent in dry diethyl ether using neat borane-methyl sulfide complex (approximately 10 M).

N-Fmoc-trans-3-(naphth-2-yl)-L-proline (Scheme I, Step 8)

Heat a solution of amino ester 7 (4.31 mmol) in 5 M hydrochloric acid (20 mL) at 100° C. overnight. Concentrate the reaction mixture in vacuo to recover the amino acid.

To a solution of the crude amino acid in acetone (22 mL), add 20% aqueous $Na_2CO_3$ until the pH of the mixture is 9–10 (pH paper). Add fmoc-O-succinimide (1.60 g, 4.74 mmol), readjust the pH, and stir the reaction mixture overnight. Carefully acidify the mixture with concentrated hydrochloric acid to about pH 2 and extract with ethyl acetate (3×100 mL). Dry the combined organic layers over $MgSO_4$, and concentrate under reduced pressure. Purify the residue by flash chromatography (97:3 dichloromethane:MeOH). TLC shows that some impurities remain. These could be removed by boiling the residue in a small amount of dichloromethane, filtering, and washing the tan solid with hexane to deliver clean product (930 mg, 2.00 mmol, 46% yield) as judged by TLC, HPLC, and NMR. NMR ($d_6$-DMSO) δ 7.95–7.80 (c, 6H); 7.68 (d, 1H, J=7.3 Hz); 7.60 (d, 1H, J=7.4 Hz); 7.50–7.34 (c, 6H); 7.25 (m, 1H), 4.39–4.15 (c, 4H); 3.70–3.48 (c, 3H); 2.29 (m, 1H); 2.14 (m, 1H).

Note: The final target can also be recrystallized from hexane/ethyl acetate. (3R,2S)-N-Fmoc-3-benzylproline and (3S, 2S)-N-Fmoc-3-benzylproline are synthesized following the procedures as set forth within Preparation 1 by employing the appropriate starting materials so as to receive the desired final product.

PREPARATION 4

Synthesis of N-methyl Ameba Resin

Mix Ameba polystyrene resin (1 equivalent of 4-(4-formyl-3-methoxyphenoxy)butyryl Novagel HL, 0.46 mmol/g, Novabiochem) and a solution of methylamine (5 equivalents) in a dichloroethane (0.3 M solution), followed by sodiumtriacetoxyborohydride (5 equivalents, anhydrous). Shake overnight. The next day add methanol to dissolve the unreacted sodiumtriacetoxyborohydride. Remove solvents by aspiration where a tubing fitted with a frit is used to prevent the resin from being aspirated. Wash three times with methanol, three times with a solution of dimethylformamide in ethanolamine (50:50), soak for 20 minutes, followed by 8 washes using dimethylformamide. Between each wash, shake for ~2 minutes. Continue aspiration until most of the free solvent is removed. Add DMSO to bring slurry to desired concentration, for distribution into a reaction vessel.

PREPARATION 5

Synthesis of R-2-bromo-3-methylbutyric Acid

Mix a cold (−10° C.) solution of $H_2SO_4$ (100 mL, 2.5 N), HBr (49%, 33 g, 200 mmol) and D-valine (12,7 g, 100 mmol) and add $NaNO_2$ (6.90 g, 100 mmol) in water (50 mL) over a period of 30 minutes. Maintain stirring at a temperature between −5° C. and −10° C. for three hours. Extract the reaction mixture with dichloromethane (2×150 mL), dry over $MgSO_4$ and concentrate to yield the title compound as a light amber oil.

EXAMPLE 1

The following eight compounds are made by the procedures as illustrated below:

| Compound Identification | Compound Structure | Compound Chemical Name |
|---|---|---|
| 1a | 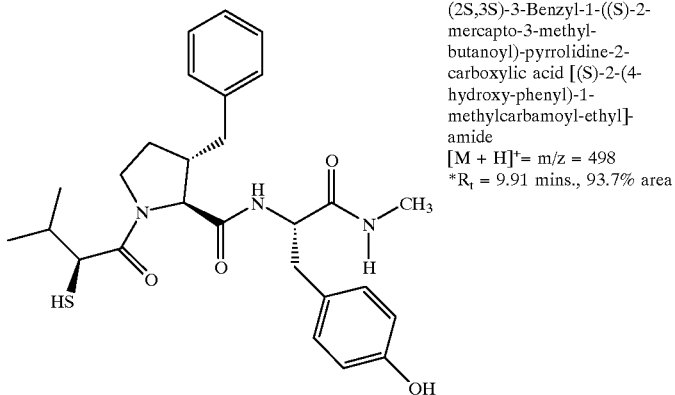 | (2S,3S)-3-Benzyl-1-((S)-2-mercapto-3-methyl-butanoyl)-pyrrolidine-2-carboxylic acid [(S)-2-(4-hydroxy-phenyl)-1-methylcarbamoyl-ethyl]-amide<br>[M + H]⁺= m/z = 498<br>*R$_t$ = 9.91 mins., 93.7% area |
| 1b | 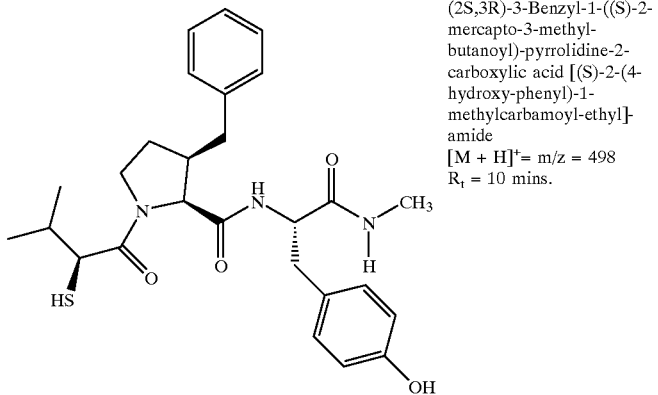 | (2S,3R)-3-Benzyl-1-((S)-2-mercapto-3-methyl-butanoyl)-pyrrolidine-2-carboxylic acid [(S)-2-(4-hydroxy-phenyl)-1-methylcarbamoyl-ethyl]-amide<br>[M + H]⁺= m/z = 498<br>R$_t$ = 10 mins. |
| 1c | 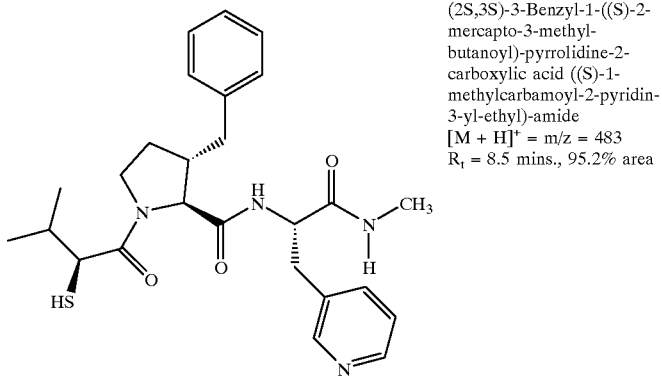 | (2S,3S)-3-Benzyl-1-((S)-2-mercapto-3-methyl-butanoyl)-pyrrolidine-2-carboxylic acid ((S)-1-methylcarbamoyl-2-pyridin-3-yl-ethyl)-amide<br>[M + H]⁺ = m/z = 483<br>R$_t$ = 8.5 mins., 95.2% area |

-continued

| Compound Identification | Compound Structure | Compound Chemical Name |
|---|---|---|
| 1d | 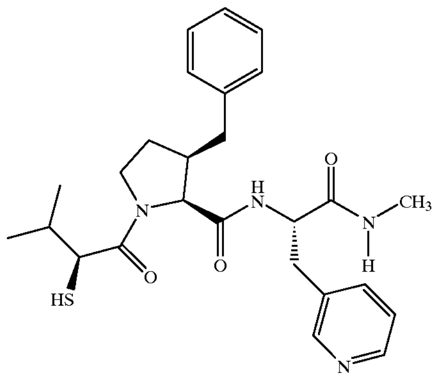 | (2S,3R)-3-Benzyl-1-((S)-2-mercapto-3-methyl-butanoyl)-pyrrolidine-2-carboxylic acid ((S)-1-methylcarbamoyl-2-pyridin-3-yl-ethyl)-amide<br>[M + H]$^+$ = m/z = 483<br>R$_t$ = 8.51 mins., 93.3% area |
| 1e | 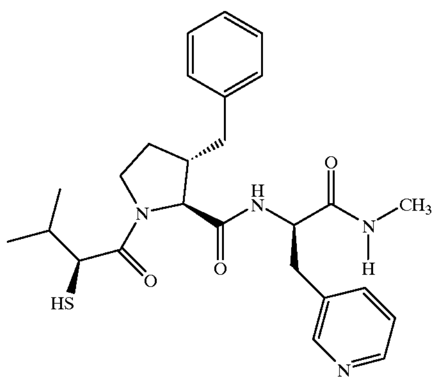 | (2S,3S)-3-Benzyl-1-((S)-2-mercapto-3-methyl-butanoyl)-pyrrolidine-2-carboxylic acid ((R)-1-methylcarbamoyl-2-pyridin-3-yl-ethyl)-amide<br>[M + H]$^+$ = m/z = 483<br>R$_t$ = 8.56 mins., 83.5% area |
| 1f | 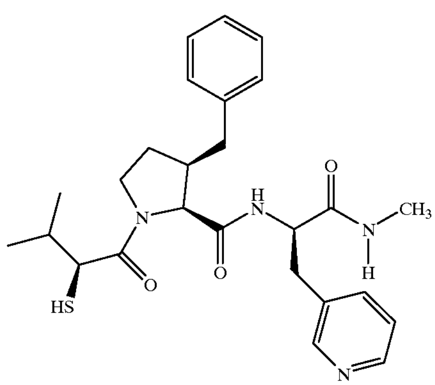 | (2S,3S)-3-Benzyl-1-((S)-2-mercapto-3-methyl-butanoyl)-pyrrolidine-2-carboxylic acid ((R)-1-methylcarbamoyl-2-pyridin-3-yl-ethyl)-amide<br>[M + H]$^+$ = m/z = 483<br>R$_t$ = 8.43 mins., 93.7% area |
| 1g | 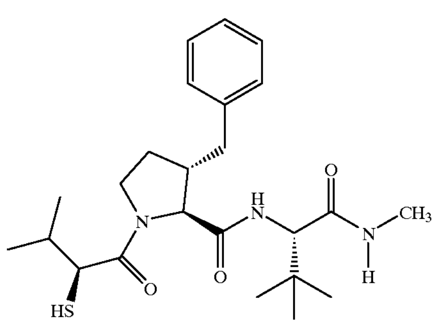 | (2S,3S)-3-Benzyl-1-((S)-2-mercapto-3-methyl-butanoyl)-pyrrolidine-2-carboxylic acid ((S)-2,2-dimethyl-1-methylcarbamoyl-propyl)-amide<br>[M + H]$^+$ = m/z = 448<br>R$_t$ = 10.35 mins., 71.4% area |

-continued

| Compound Identification | Compound Structure | Compound Chemical Name |
|---|---|---|
| 1h | 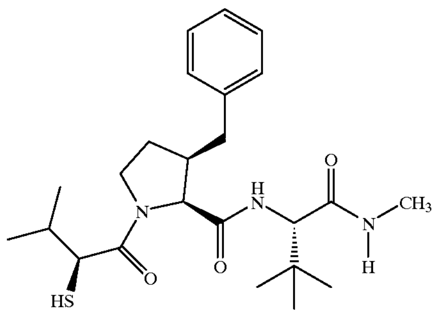 | (2S,3R)-3-Benzyl-1-((S)-2-mercapto-3-methyl-butanoyl)-pyrrolidine-2-carboxylic acid ((S)-2,2-dimethyl-1-methylcarbamoyl-propyl)-amide<br>$[M + H]^+$ = m/z = 448<br>$R_t$ = 10.8 mins., 38% area and 11.2 mins., 55.9% |

*$R_t$ = Retention Time

Step 1: Preparation of Resin:

In a 20 mL fritted syringe, treat ~1.6 g of N-methyl Ameba resin (ca 0.7 mm/g) twice with a solution of 10 mL 20% hydroxyl amine in DMF. Wash the resin extensively with 5×10 mL DMF, 5×10 mL MeOH, and 5×10 mL THF. Dry the resin under Nitrogen and divide into eight, 200 mg (theoretically 0.14 mm reaction sites) portions and place into eight 5 mL fritted syringes. Identify the syringes with S-L-Tyr, R-L-Tyr, S-L-pyrAla, R-L-pyrAla, S-D-pyrAla, R-D-pyrAla, S-L-tBuGly, R-L-tBuGly. The R and S designations identify which 3-benzylproline is used in the second coupling step (4).

Step 2: First Coupling:

The R and S syringes for each amino acid Step (2) coupling are treated identically as follows: Remove the plungers and treat the first two syringes with 230 mg (0.5 mmol) of N-FMOC-O-tBuTyr-OH (FW=459.5) and 76 mg (0.5 mm) of HOBT.H$_2$O (FW=153). In a similar fashion, treat the other pairs of syringes with 194 mg of N-FMOC-L-3-pyrAla-OH (FW=388), 194 mg of N-FMOC-D-3-pyrAla-OH, and 184 mg of N-FMOC-L-tBuBly-OH along with 76 mg of HOBT each (source of FMOC amino acids is Advanced Chem Tech). Prepare a solution of 630 mg (5.0 mm) DIC (FW=126) in 20 mL of dry DMF. Draw 2.2 mL of this solution into each syringe and cap the needles. Shake the syringes for 18 hrs. At the end of this period, force the reagents out of the syringes and wash each syringe with 3×3 mL DMF.

Step 3: Deprotection/FMOC Reading:

Remove the excess FMOC amino acids. Treat each syringe with two, 2.5 mL portions of 20% piperidine in DMF for 20 minutes each followed by a washing with 5×2.5 mL DMF, 3×2.5 mL MeOH, and 5×2.5 mL THF. Dry the resin under Nitrogen. Transfer all washes to a 50 mL Falcon tube and dilute to a volume of 50 mL. Transfer 100 μL of this solution to a 10 mL Falcon tube and dilute to a volume of 10 mL. Use UV-VIS analysis of the solution to calculate the finctionalization of the resin. These results are given as FMOC-1 in Table I.

TABLE I

| Compound Identification | Label from Step 1 | FMOC-1[1] (mmol/g) | FMOC-2[1] (mmol/g) |
|---|---|---|---|
| 1a | S-L-Tyr | 0.27 | 0.35 |
| 1b | R-L-Tyr | 0.26 | 0.32 |
| 1c | S-L-pyrAla | 0.29 | 0.37 |
| 1d | R-L-pyrAla | 0.29 | 0.38 |
| 1e | S-D-pyrAla | 0.31 | 0.35 |
| 1f | R-D-pyrAla | 0.31 | 0.35 |
| 1g | S-L-tBuGly | 0.25 | 0.34 |
| 1h | R-L-tBuGly | 0.30 | 0.35 |

[1]Sample Calculation for typical FMOC results:

$$\text{Resin Substitution (mmol/g)} = \frac{\text{Absorbance} \times \text{Volume of Solution Used} \times \text{Dilution Factor}}{\text{Extinction Coefficient} \times \text{Resin Amount Used (g)}}$$

Volume of Solution Used = 50 mL
Dilution Factor = 100
Extinction Coefficient = 8100

Step 4: Coupling of Substituted Prolines:

The syringes with the initial R identification are all treated identically as follows: Remove the plungers and add 214 mg (0.5 mm) of N-FMOC-L-3-R-benzylproline (FW=427.5) and 68 mg (0.5 mm) of HOAT (FW=136) to each of the dried resins. Prepare a solution of 630 mg (5.0 mm) DIC (FW=126) in 20 mL of dry DMF. Draw 2.2 mL of this solution into each syringe and cap the needles. Shake the syringes for 18 hrs. At the end of this period, force the reagents out of the syringes and wash each syringe with 3×3 mL DMF.

Step 5: Deprotection/FMOC Reading:

Remove the excess FMOC amino acids. Treat each syringe with two, 2.5 mL portions of 20% piperidine in DMF for 20 minutes each followed by a washing with 5×2.5 mL DMF, 3×2.5 mL MeOH, and 5×2.5 mL THF. Drythe resin under Nitrogen. Transfer all washes to a 50 mL Falcon tube and dilute to a volume of 50 mL. Transfer 100 μL of this solution to a 10 mL Falcon tube and dilute to a volume of 10 mL. Use UV-VIS analysis of the solution to calculate the functionalization of the resin. These results are given as FMOC-2 in Table I.

Step 6: Coupling of Bromo Acid:

Prepare a solution of 1.49g (10 mm) of (R)-2-bromo-3-methylbutyric acid in 10 mg of DMF. In addition, prepare a solution of 1.81g (10 mm) of DIC in 10 mL of DMF. Into each syringe, draw in 1.2 mL of each solution prepared. Cap the syringes and shake for 4 hours. Wash each syringe with 3×2 mL DMF followed by 5×2 mL DCM. Dry the resin under nitrogen.

Step 7: Displacement with Thiol Acetic Acid Salt:

Prepare a 20 mL solution of a 0.3 M solution of potassium thioacetate (Aldrich #24,177–6) in deoxygenated NMP and further degass. Optionally, thioacetic acid in cesium carbonate could be used. Into each syringe, draw up 2.2 mL of the solution, cap the syringes and shake for 2 hrs. Wash the resins with 2.5 mL of 1:1 DMF/DCM, 1:1 DMF/cold MeOH, and 2.5 mL of cold MeOH.

Step 8: Cleavage of Thiol Ester:

Deoxygenate methanol by bubbling nitrogen vigorously for 15 minutes. Treat each syringe with 2 mL of 2M dimethyl amine in THF. Shake for 10 minutes and wash each syringe with 2× cold MeOH, 2 mL 5% aqueous HOAc, 2×2 mL cold MeOH, and 5×2 mL degassed DCM.

Step 9: Cleavage from Resin:

Prepare a cocktail of 36 mL TFA, 2.8 mL of water, 600 µL of 2-mercaptoethanol, and 600 µL of anisole. Degass the cocktail with nitrogen for 5 minutes and treat each syringe with 2.5 mL of the cocktail, cap the syringes and shake for 1 hr. Transfer the cleavage solution to a 20 mL vial and expose each syringe to 1.5 mL of the cleavage solution for an additional 30 min. Combine the extracts and concentrate under a stream of nitrogen.

Step 10: Purification:

Evaluate each extract by LC/MS and this indicates that the products have been generated in relatively pure form (>50%). Use a gradient of 2–85% acetonitile/water over 15 minutes. The retention times indicate that the products elute off the column at >50% acetonitrile. Set up a waters Delta Prep using a 20–100% gradient over 40 minutes. Degass the solvents extensively. Dissolve each in degassed MeOH (0.5 mL) followed by acetonitrile (4.5 mL), and then water (5mL). Then purify the samples. Collect several fractions. The LC traces show the major peaks followed by minor ones. LC/MS confirms which fractions contain the desired material. Concentrate these fractions under a stream of nitrogen and transfer to tared 1 mL vials. Perform a final concentration and dry on the lyophylizer to give the indicated yields.

LC/MS conditions are as follows: Column: Keystone Betasil C18 Javelin, 2×30 mm, Solvent: Gradient over 15 minutes of 2–85% acetonitrile in water, Flow: 0.7 mL/min., Detection: UV at 220 nm.

Waters Delta Prep Conditions are as follows: Column: Waters Protein and Peptide C18 column, Solvent: Grandient over 40 minutes, 20–1 00% degassed methanol in acetonitrile and water, Flow: 20 mL/min., Detection: UV at 270 nm.

The present invention provides a method of inhibiting matrix metalloproteinase (MMP) to a patient in need thereof comprising administering to the patient an effective matrix metalloproteinase inhibiting amount of a compound of formula (1).

As used herein, the term "patient" refers to warm-blooded animals or mammals, including guinea pigs, dogs, cats, rats, mice, hamsters, rabbits and primates, including humans. A patient is in need of treatment to inhibit MMP when it would be beneficial to the patient to reduce the physiological effect of active MMP. For example, a patient is in need of treatment to inhibit MMP when a patient is suffering from a disease state characterized by excessive tissue disruption or tissue degradation, such as, but not limited to, a neoplastic disease state or cancer; rheumatoid arthritis; osteoarthritis; cardiovascular disorders, such as atherosclerosis; corneal ulceration; dental diseases, such as gingivitis or periodontal disease; and neurological disorders, such as multiple sclerosis; chronic inflammatory disorders, such as emphysema and especially smoking-induced emphysema.

The identification of those patients who are in need of treatment to inhibit MMP is well within the ability and knowledge of one skilled in the art. A clinician skilled in the art can readily identify, by the use of clinical tests, physical examination and medical/family history, those patients who are suffering ftom disease states characterized by excessive tissue disruption or tissue degradation.

An "effective matrix metalloproteinase inhibiting amount" of a compound of formula (1) is an amount which is effective, upon single or multiple dose administration to the patient, in providing relief of symptoms associated with MMP and is thus effective in inhibiting MMP-induced tissue disruption and/or MMP-induced tissue degradation. As used herein, "relief of symptoms" of MMP-mediated conditions refers to decrease in severity over that expected in the absence of treatment and does not necessarily indicate a total elimination or cure of the disease. Relief of symptoms is also intended to include prophylaxis.

An effective matrix metalloproteinase inhibiting dose can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

An effective matrix metalloproteinase inhibiting amount of a compound of formula (1) will generally vary from about 0.1 milligram per kilogram of body weight per day (mg/kg/day) to about 300 milligrams per kilogram of body weight per day (mg/kg/day). A daily dose of from about 1 mg/kg to about 100 mg/kg is preferred.

A neoplastic disease state refers to an abnormal state or condition characterized by rapidly proliferating cell growth or neoplasm. Neoplastic disease states for which treatment with a compound of formula (1) will be particularly useful include: Leukemias, such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkin's Disease. Neoplastic disease states for which treatment with a compound of formula (1) will be particularly preferred include carcinomas and adenocarcinomas, particularly of the breast, prostate and lung. Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: emphysema, chronic bronchitis, asthma, and chronic inflammation, and especially smoking-induced emphysema.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, topically, intranasally, rectally, inhalation, and the like. Oral and inhalation administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, gels, ointments, aerosol or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0. 1% of a compound of the invention, but may be varied to be between 0.1% and about 50% of the weight thereof. The amount of the active ingredient present in such compositions is such that a suitable dosage will be obtained. Preferred compositions and preparations are able to be determined by one skilled in the art.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of the present invention may also be administered by inhalation, such as by aerosol or dry powder. Delivery may be by a liquefied or compressed gas or a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The MMP inhibitors of the present invention can be evaluated by the procedures that follow.

EXAMPLE A
Source and Activation of proMMP-1

ProMMP-1 (EC 3.4.24.7; interstitial collagenase) was purified from culture medium of human rheumatoid synovial fibroblasts stimulated with macrophage-conditioned medium according to Okada, Y. et al., *J. Biol. Chem.* 261, 14245–14255 (1986). The active MMP-1 was obtained by treatment of proMMP-1 with trypsin (5 µg/mL) at 37° C. for 30 minutes, followed by addition of soybean trypsin inhibitor (50 µg/mL).

Determination of Inhibition Constant ($K_i$) for MMP-1 The activated MMP-1 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in 2.0 mL of assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF. For determination of $K_i$ values for MMP-1 inhibitors, a series of intermediate inhibitor solutions were prepared in DMF and 1 or 2 µL of the diluted inhibitor solution was mixed with 1 µL of 2 mM substrate solution in DMF in a quartz cuvette containing 2 mL of assay buffer. The enzyme (10 µL of 0.2 µM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 µM (<<Km) and [MMP-1]=0.8 nM. Under these conditions, the measured $K_i$ app is close to true $K_i$.

Calculation of $K_i$ Values

The $K_i$ for a competitive inhibitor is calculated using: $v_0/v_i=(1+[I]/K_{i,\,app})$ and $K_i=K_{i,\,app}/(1+[S]/K_m)$, where $v_0$ is the initial rate in the absence of inhibitor, vi is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

EXAMPLE B
Source and Activation of proMMP-2

Recombinant MMP-2 was purified from the fermentation broth of yeast *Pichia pastoris* that carries the integrated MMP-2 gene into its chromosome. In brief, the full-length cDNA for MMP-2 was obtained by reverse transcription of RNA from human melanoma A375M cell line by the reverse transcriptase polymerase chain reaction (RT-PCR) using sequence specific oligonucleotides. The nucleotide sequence was confirmed by Taq cycle sequencing. The cDNA was ligated into the *Pichia pastoris* expression vector pHIL-D2 in such a way that the expression of pro-MMP-2 is under the control of the methanol inducible alcohol oxidase promoter. The expression construct was digested with either SalI or NsiI and used to transform the *Pichia pastoris* strains KM71 and SMD1 168. A large-scale culture of a selected clone designated 24S was performed in a high cell density fermentor and the recombinant MMP-2 was purified from the culture supernatant by gelatin-sepharose 4B (Pharmacia). The enzyme is sufficiently pure at this stage for routine measurement of inhibition. If desired, however, the enzyme may be further purified by AcA 44 gel filtration (Spectra).

Determination of Inhibition Constant ($K_i$) for MMP-2

The active MMP-2 was obtained by activation of proMMP-2 at 37° C. for 1 h with 4-aminophenylmercuric acetate which was then removed by a Sephadex G-50 spin column. The enzyme is assayed using a fluorogenic substrate, Mca-Pro-Leu-Gly-Leu-Dpa-Ala-Arg-NH$_2$, at 37° C. in 2.0 mL of assay buffer containing 50 mM Tris, pH 7.6, 0.2 M sodium chloride, 50 mM calcium chloride, 0.02% Brij-35, and 50 µM β-mercaptoethanol. The increase in fluorescence is monitored ($\lambda_{ex}$ 328 nm, $\lambda_{em}$ 393 nm). Substrate and inhibitor stock solutions are made in DMF. The enzyme is added at the last to start the reaction. For routine measurement of a $K_i$ value for a reversible, competitive inhibitor, the initial rates in the presence of at least four inhibitor concentrations (two inhibitor concentrations above $K_i$ and two below $K_i$) are measured using [S]=1 µM (<<$K_m$) and [MMP-2]=0.4 nM. Under these conditions, the measured $K_{i,\,app}$ is close to true $K_i$.

EXAMPLE C
Source and Activation of proMMP-3

ProMMP-3 (EC 3.4.24.17; Stromelysin-1) was purified from culture medium of human rheumatoid synovial fibroblasts stimulated with macrophage-conditioned medium according to Okada, Y. et al., *J. Biol. Chem.* 261, 14245–14255 (1986). The active MMP-3 was obtained by treatment of proMMP-3 with trypsin (5 µg/mL) at 37° C. for 30 minutes, followed by addition of soybean trypsin inhibitor (50 µg/mL). Aliquots of the activated MMP-3 were stored at −20° C.

Determination of Inhibition Constant ($K_i$) for MMP-3

The activated MMP-3 is assayed using a fluorogenic substrate, Mca-Pro-Leu-Gly-Leu-Dpa-Ala-Arg-NH$_2$, Knight, C.G. et al., *FEBS Lett.* 296, 263–266 (1992), at 37° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF and 0.1 % HCl-DMF, respectively. For determination of $K_i$ values for MMP-3 inhibitors, a series of intermediate inhibitor solutions were prepared in 0.1% HCl-DMF and 1 or 2 µL of the diluted inhibitor solution was mixed with 1 µL of 2 mM substrate solution in DMF in a quartz cuvette containing 2 mL of assay buffer. The enzyme (10 µL of 0.2 µM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 µM (<<Km) and [MMP-3]=1 nM. Under these conditions, the measured $K_{i,\,app}$ is close to true $K_i$.

Calculation of $K_i$ Values

The K, for a competitive inhibitor is calculated using: $V_0/v_i=(1+[I]/K_{i,\,app})$ and $K_i=K_{i,\,app}/(1+[S]/Km)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

EXAMPLE D

The MMP-8 data was determined according to Knight C. G. et al., *Febs Lett*, 296, 263–266 (1992), "A novel coumarin-labelled peptide for sensitive continuous assays of the matrix metalloproteinases" in the modification of K. U. Weithmann et al., *Inflamm. Res.* 46 (7), 246–252 (1997), "Effects of tiaprofenic acid on urinary pyridinium crosslinks in adjuvant arthritic rats: Comparison and doxycycline effects on human matrix metalloproteinases and cellular cytokine generation in vitro" as follows:

Enzyme activity of MMP was determined in 96 well titer plate format in a luminescence spectrometer (LS 50B, Perkin Elmer, Langen, FRG), using the quenched fluorigenic substrate 7-methoxycoumarin-4-yl) acetyl-pro-leu-gly-leu-3-(2',4'-dinitrophenyl)-L-2,3-diaminopropionyl-ala-arg-NH$_2$ (λex=328 nm, λem=393 nm), available from Bachem, Heidelberg, FRG. Each well contained: 70 µl buffer (0.1 mol/l tris/HCl, pH=7.5; 0.1 mol/l NaCl; 0.01 mol/l CaCl$_2$, 0.05% Brij 35™), 10 µl enzyme, and 10 µl drug in 10%DMSO. After preincubation for 15 min at room temperature the reaction was started by addition of 10 µl substrate (1 mmol/l in 10% DMSO). Initial velocity of enzymatic reaction was determined without drug (=100%) or, resp. with different drug concentrations.

EXAMPLE E

Source of MMP-12 (Macrophage Metalloelastase)

MMP-12 (EC 3.4.24.65) was cloned, expressed and purified according to Shapiro, S. D. et al., *J Biol. Chem.* 268, 23824–23829 (1993). Autoactivation resulted in the fully processed active form of the enzyme. Aliquots of MMP-12 were stored at –70 C.

Determination of the inhibition constant ($K_i$) for MMP-12.

The potency of inhibitors of MMP-12 was measured using either quartz cuvettes or microtiter plates. The activity of MMP-12 was measured using a fluorogenic substrate, Mca-Pro-Leu-Gly-Leu-Dpa-Ala-Arg-NH$_2$, Knight, C. G. et al., *FEBS Lett.* 296, 263–266 (1992), at25° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-12 was monitored with a Perkin-Elmer LS50B Fluorimeter (lex 328 nm, lem 393 nm, excitation slit 2.5, emission slit 10) for the cuvette assay and with a Molecular Devices Fmax fluorescence plate reader ($\lambda_{ex}$ 320 nm, $\lambda_{em}$ 405 nm) for the microtiter plate assay. Substrate and inhibitor stock solutions were made in N,N-dimethylformamide (DMF) and 0.1% HCl-DMF, respectively.

$K_i$ values were determined using the cuvette method by preparing a series of intermediate inhibitors solutions in 0.1% HCl-DMF and mixing the inhibitor with substrate (final concentration 2 mM) in a quartz cuvette containing 2 ml of assay buffer. MMP-12 was added to start the reaction at a concentration of 2 nM and progress curves were generated. For routine measurement of a $K_i$ value for a reversible competitive inhibitor, the initial rates in the presence of at least four inhibitor concentrations (two concentrations above and two concentrations below the $K_i$) were measured [S]=2 mM (<<$K_m$) and [MMP-12]=2 nM. Under these conditions, the measured $K_{i,app}$ is close to the true $K_i$.

$K_i$ values were determined using the microtiter plate method in a manner similar to that described for the cuvette method with some modifications. Four different inhibitor concentrations (50 ml in assay buffer)of each compound were added to separate wells of a microtiter plate and substrate was added (100 ml) to get a final concentration of 4 mM. MMP-12 was added to a final concentration of 2 nM (50 ml) to start the reaction. Cleavage of substrate was recorded every 30 seconds for 30 minutes and progress curves were generated.

Calculation of $K_i$ Values

The $K_i$ for a competitive inhibitor is calculated using: $V_0/v_i=(1+[I]/K_{i, app})$ and $K_i=K_{i, app}/(1+[S]/Km)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

$K_i$ values showing inhibition of MMP-1, MMP-2, MMP-3, MMP-8, MMP-13, and MMP-14, for representative compounds of the present invention are found in Table II. The MMP values in Table I below are determined by the methods of present Examples A–D.

TABLE II

| Compound (Example Number) | MMP[1] $K_{i\ app}$ (nM) | MMP-8 $K_{i\ app}$ (nM) |
|---|---|---|
| 1a | >10,000 | >10,000 |
| 1b | >10,000 | 3,000 |
| 1c | >10,000 | 9,000 |
| 1d | >10,000 | 4,000 |
| 1e | >10,000 | >10,000 |
| 1f | >10,000 | >10,000 |
| 1g | >10,000 | >10,000 |
| 1h | >10,000 | 3,000 |

[1]Results are identical for MMP-1, MMP-2, MMP-3, MMP-13 and MMP-14.

What is claimed is:

1. A compound of the formula

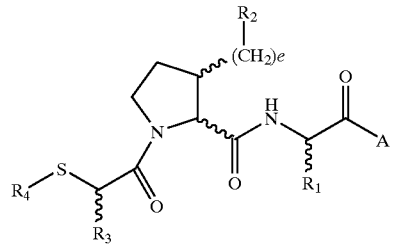

wherein e is an integer from 0 to 2;

A is selected from the group consisting of —OH and —NRR';

wherein

R and R' are independently selected from the group consisting of hydrogen and $C_1$–$C_6$ alkyl or R and R' taken together with the nitrogen atom to which they are attached form a N-morpholino, N-piperidino, N-pyrrolidino, or N-isoindolyl;

$R_1$ is selected from the group consisting of hydrogen, $C_1$–$C_6$ alkyl, —$(CH_2)_a$—$CO_2R_5$, —$(CH_2)_a$—$C(O)NH_2$, —$(CH_2)_4NH_2$, —$(CH_2)_3$—NH—C(NH)NH$_2$, —$(CH_2)_2$—S(O)$_b$—CH$_3$, —CH$_2$—OH, —CH(OH)CH$_3$, —CH$_2$—SH, —$(CH_2)_d$—Ar$_1$, and —CH$_2$—Ar$_2$;

wherein a is 1 or 2;

b is 0, 1,or 2;

d is an integer from 0 to 4;

$R_5$ is selected from the group consisting of hydrogen, $C_1$–$C_4$ alkyl, and benzyl;

Ar$_1$ is a radical selected from the group consisting of

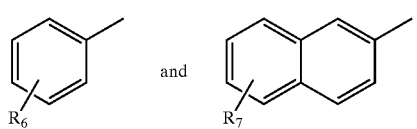

wherein $R_6$ is from 1 to 2 substituents independently selected from the group consisting of hydrogen, halogen, $C_1$–$C_4$ alkyl, hydroxy, and $C_1$–$C_4$ alkoxy;

$R_7$ is selected from the group consisting of hydrogen, halogen, $C_1$–$C_4$ alkyl, and $C_1$–$C_4$ alkoxy;

Ar$_2$ is a radical selected from the group consisting of

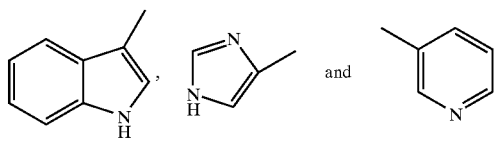

R$_2$ is a radical selected from the group consisting of

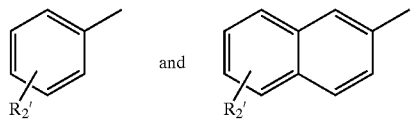

wherein wherein

R$_{2'}$ is from 1 to 2 substituents selected from the group consisting of hydrogen, halogen, C$_1$–C$_4$ alkyl, and C$_1$–C$_4$ alkoxy;

R$_3$ is selected from the group consisting of C$_1$–C$_6$ alkyl, —(CH$_2$)$_m$—W, —(CH$_2$)$_p$—Ar$_3$, —(CH$_2$)$_k$—CO$_2$R$_9$, —(CH$_2$)$_m$—NR$_8$SO$_2$—Y$_1$, and —(CH$_2$)$_m$—Z—Q wherein m is an integer from 2 to 8;

p is an integer from 0–10;

k is an integer from 1 to 9;

W is phthalimido;

Ar$_3$ is selected from the group consisting of

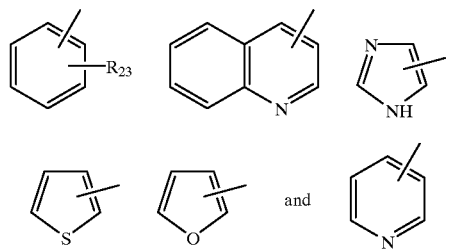

wherein

R$_{23}$ is from 1 to 2 substituents independently selected from the group consisting of hydrogen, halogen, C$_1$–C$_4$ alkyl, and C$_1$–C$_4$ alkoxy;

R$_{8'}$ is hydrogen or C$_1$–C$_6$ alkyl;

R$_9$ is hydrogen or C$_1$–C$_6$ alkyl;

Y$_1$ is selected from the group consisting of hydrogen, —(CH$_2$)$_j$—Ar$_4$, and —N(R$_{24}$)$_2$ wherein j is 0 or 1;

R$_{24}$ each time selected is independently hydrogen or C$_1$–C$_6$ alkyl or are taken together with the nitrogen to which they are attached to form N-morpholino, N-piperidino, N-pyrrolidino, or N-isoindolyl;

Ar$_4$ is

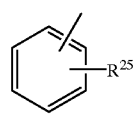

wherein

R$_{25}$ is from 1 to 3 substituents independently selected from the group consisting of hydrogen, halogen, C$_1$–C$_4$ alkyl, and C$_1$–C$_4$ alkoxy;

Z is selected from the group consisting of —O—, —NR$_8$—, —C(O)NR$_8$—, —NR$_8$C(O)—, —NR$_8$C(O)NH—, —NR$_8$C(O)O—, and —OC(O)NH—;

wherein

R$_8$ is hydrogen or C$_1$–C$_6$ alkyl;

Q is selected from the group consisting of hydrogen, —(CH$_2$)$_n$—Y$_2$, and —(CH$_2$)$_x$—Y$_3$;

wherein n is an integer from 0 to 4;

Y$_2$ is selected from the group consisting of hydrogen, —(CH$_2$)$_h$—Ar$_5$ and —(CH$_2$)$_t$—C(O)OR$_{27}$ wherein Ar$_5$ is selected from the group consisting of

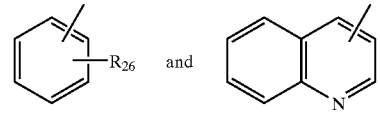

wherein

R$_{26}$ is from 1 to 3 substituents independently selected from the group consisting of hydrogen, halogen, C$_1$–C$_4$ alkyl, and C$_1$–C$_4$ alkoxy;

h is an integer from 0 to 6;

t is an integer from 1 to 6;

R$_{27}$ is hydrogen or C$_1$–C$_6$ alkyl;

x is an integer from 2 to 4;

Y$_3$ is selected from the group consisting of —N(R$_{28}$)$_2$, N-morpholino, N-piperidino, N-pyrrolidino, and N-isoindolyl;

wherein

R$_{28}$ each time taken is independently selected from the group consisting of hydrogen and C$_1$–C$_6$ alkyl;

R$_4$ is selected from the group consisting of hydrogen, —C(O)R$_{10}$, —C(O)—(CH$_2$)$_q$—K and —S—G wherein R$_{10}$ is selected from the group consisting of hydrogen, C$_1$–C$_4$ alkyl, phenyl, and benzyl;

q is 0, 1, or 2;

K is selected from the group consisting of

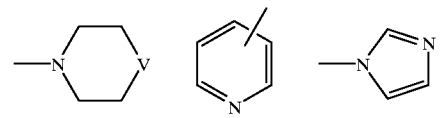

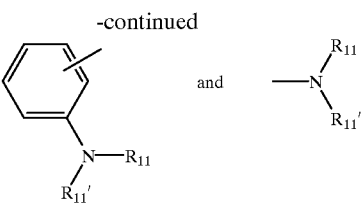

wherein
V is selected from the group consisting of a bond, —CH$_2$—, —O—, —S(O)$_r$—, —NR$_{21}$—, and —NC(O)R$_{22}$—;
wherein
r is 0, 1, or 2;
R$_{21}$ is selected from the group consisting of hydrogen, C$_1$–C$_4$ alkyl, and benzyl;
R$_{22}$ is selected from the group consisting of hydrogen, —CF$_3$, C$_1$–C$_{10}$ alkyl, phenyl, and benzyl;
R$_{11}$ is selected from the group consisting of hydrogen, C$_1$–C$_4$ alkyl, and benzyl;
R$_{11'}$ is selected from the group consisting of hydrogen, C$_1$–C$_4$ alkyl, and benzyl;
G is selected from the group consisting of

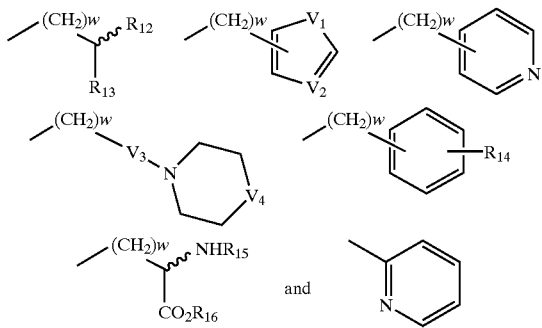

wherein
w is an integer from 1 to 3;
R$_{12}$ is selected from the group consisting of hydrogen, C$_1$–C$_6$ alkyl, —CH$_2$CH$_2$S(O)$_f$CH$_3$, and benzyl;
wherein f is 0, 1, or 2;
R$_{13}$ is selected from the group consisting of hydrogen, hydroxy, amino, C$_1$–C$_6$ alkyl, N-methylamino, N,N-dimethylamino, —CO$_2$R$_{17}$, and —OC(O)R$_{18}$;
wherein
R$_{17}$ is hydrogen, —CH$_2$O—C(O)C(CH$_3$)$_3$, C$_1$–C$_4$ alkyl, benzyl, or diphenylmethyl;
R$_{18}$ is hydrogen, C$_1$–C$_6$ alkyl or phenyl;
R$_{14}$ is 1 or 2 substituents independently selected from the group consisting of hydrogen, C$_1$–C$_4$ alkyl, C$_1$–C$_4$ alkoxy, or halogen;
V$_1$ is selected from the group consisting of —O—, —S—, and —NH—;
V$_2$ is selected from the group consisting of —N— and —CH—;
V$_3$ is selected from the group consisting of a bond and —C(O)—;
V$_4$ is selected from the group consisting of —O—, —S—, —NR$_{19}$—, and —NC(O)R$_{20}$—;
wherein
R$_{19}$ is hydrogen, C$_1$–C$_4$ alkyl, or benzyl;
R$_{20}$ is hydrogen, —CF$_3$, C$_1$–C$_{10}$ alkyl, or benzyl;
R$_{15}$ is selected from the group consisting of hydrogen, C$_1$–C$_6$ alkyl and benzyl;

R$_{16}$ is selected from the group consisting of hydrogen and C$_1$–C$_4$ alkyl; and stereoisomers, pharmaceutically acceptable salt, and hydrate thereof.

2. A compound of claim 1 wherein R$_1$ is a —CH$_2$)$_d$—Ar$_1$ group.

3. A compound of claim 2 wherein d is 1 or 2 and Ar$_1$ is phenyl or substituted phenyl.

4. A compound of claim 1 wherein R$_4$ is —C(O)R$_{10}$.

5. A compound of claim 4 wherein R$_{10}$ is C$_1$–C$_4$ alkyl.

6. A compound of claim 1 wherein A is —OH.

7. A compound of claim 1 wherein A is —NRR'.

8. A compound of claim 7 wherein R is hydrogen and R'.

9. A compound of claim 1 wherein R$_4$ is —SG.

10. A compound according to claim 1 wherein the compound is (2S,3S)-3-Benzyl-1-((S)-2-mercapto-3-methyl-butanoyl)-pyrrolidine-2-carboxylic acid [(S)-2-(4-hydroxy-phenyl)-1-methylcarbamoyl-ethyl]-amide.

11. A compound according to claim 1 wherein the compound is (2S,3R)-3-Benzyl-1-((S)-2-mercapto-3-methyl-butanoyl)-pyrrolidine-2-carboxylic acid [(S)-2-(4-hydroxy-phenyl)-1-methylcarbamoyl-ethyl]-amide.

12. A compound according to claim 1 wherein the compound is (2S,3S)-3-Benzyl-1-((S)-2-mercapto-3-methyl-butanoyl)-pyrrolidine-2-carboxylic acid ((S)-1-methylcarbamoyl-2-pyridin-3-yl-ethyl)-amide.

13. A compound according to claim 1 wherein the compound is (2S,3R)-3-Benzyl-1-((S)-2-mercapto-3-methyl-butanoyl)-pyrrolidine-2-carboxylic acid ((S)-1-methylcarbamoyl-2-pyridin-3-yl-ethyl)-amide.

14. A compound according to claim 1 wherein the compound is (2S,3S)-3-Benzyl-1-((S)-2-mercapto-3-methyl-butanoyl)-pyrrolidine-2-carboxylic acid ((R)-1-methylcarbamoyl-2-pyridin-3-yl-ethyl)-amide.

15. A compound according to claim 1 wherein the compound is (2S,3R)-3-Benzyl-1-((S)-2-mercapto-3-methyl-butanoyl)-pyrrolidine-2-carboxylic acid ((R)-1-methylcarbamoyl-2-pyridin-3-yl-ethyl)-amide.

16. A compound according to claim 1 wherein the compound is (2S,3S)-3-Benzyl-1-((S)-2-mercapto-3-methyl-butanoyl)-pyrrolidine-2-carboxylic acid ((S)-2,2-dimethyl-1-methylcarbamoyl-propyl)-amide.

17. A compound according to claim 1 wherein the compound is (2S,3R)-3-Benzyl-1-((S)-2-mercapto-3-methyl-butanoyl)-pyrrolidine-2-carboxylic acid ((S)-2,2-dimethyl-1-methylcarbamoyl-propyl)-amide.

18. A compound according to claim 1 wherein the compound is 3-Benzyl-1-(2-mercapto-3-methyl-butanoyl)-pyrrolidine-2-carboxylic acid amide; compound with 2-methylpentane.

19. A compound according to claim 1 wherein the compound is 3-Benzyl-1-(2-mercapto-3-methyl-butanoyl)-pyrrolidine-2-carboxlic acid amide; compound with 2,4-dimethyl-pentanoic acid methylamide.

20. A compound according to claim 1 wherein the compound is 2-({1-[3-Benzyl-1-(2-mercapto-3-methyl-butanoyl)-pyrrolidin-2-yl]-methanoyl}-amino)-4-methyl-pentanoic acid.

21. A compound according to claim 1 wherein the compound is 3-Benzyl-1-(2-mercapto-3-methyl-butanoyl)-pyrrolidine-2-carboxylic acid phenethyl-amide.

22. A compound according to claim 1 wherein the compound is 3-Benzyl-1-(2-mercapto-3-methyl-butanoyl)-pyrrolidine-2-carboxylic acid (1-methylcarbamoyl-2-phenylethyl)-amide.

23. A compound according to claim 1 wherein the compound is 2-({1-[3-Benzyl-1-(2-mercapto-3-methyl-butanoyl)-pyrrolidin-2-yl]-methanoyl} -amino)-3-phenyl-propionic acid.

24. A compound according to claim 1 wherein the compound is 3-Benzyl-1-(2-mercapto-3-methyl-butanoyl)-pyrrolidine-2-carboxylic acid (2-pyridin-3-yl-ethyl)-amide.

25. A compound according to claim 1 wherein the compound is 2-({1-[3-Benzyl-1-(2-mercapto-3-methyl-butanoyl)-pyrrolidin-2-yl]-methanoyl}-amino)-3-pyridin-3-yl-propionic acid.

26. A compound according to claim 1 wherein the compound is 3-Benzyl-1-(2-mercapto-3-methyl-butanoyl)-pyrrolidine-2-carboxylic acid isobutyl-amide.

27. A compound according to claim 1 wherein the compound is 3-Benzyl-1-(2-mercapto-3-methyl-butanoyl)-pyrrolidine-2-carboxylic acid (2-methyl-1-methylcarbamoyl-propyl)-amide.

28. A compound according to claim 1 wherein the compound is 2-({1-[3-Benzyl-1-(2-mercapto-3-methyl-butanoyl)-pyrrolidin-2-yl]-methanoyl}-amino)-3-methyl-butyric acid.

29. A pharmaceutical composition comprising a compound of claim 1 and a pharmaceutically acceptable carrier.

30. A method of treating MMP-induced disease states selected from the group consisting of excessive tissue disruption, tissue degradation, rheumatoid arthritis, osteoarthritis, cardiovascular disorders, atherosclerosis, corneal ulceration, dental diseases, gingivitis, periodontal disease, neurological disorders, multiple sclerosis, chronic inflammatory disorders, emphysema, smoking-induced emphysema, a neoplastic disease state or cancer selected from leukemias, acute lymphoblastic, chronic lymphocytic, acute myeloblastic, chronic myelocytic, carcinomas and adenocarcinomas of the cervix, oesophagus, stomach, small intestines, colon, small cell lungs, large cell lungs, breast and prostate, sarcomas, oesteroma, osteosarcoma, lipoma, liposarcoma, hemangioma, hemangiosarcoma, melanomas, amelanotic melanomas, melanotic melanomas, neoplasias, carcinosarcoma, lymphoid tissue type, follicullar reticulum, cell sarcoma and Hodgkin's Disease which comprises administering to the patient and effective matrix metalloproteinase inhibiting amount of a compound of claim 1.

31. A method of treating MMP-induced tissue disruption or tissue degradation disease states selected from the group consisting of rheumatoid arthritis, osteoarthritis, cardiovascular disorders, atherosclerosis, corneal ulceration, dental diseases, gingivitis, periodontal disease, neurological disorders, multiple sclerosis, chronic inflammatory disorders, emphysema, and smoking-induced emphysema which comprises administering to the patient an effective matrix metallproteinase inhibiting amount of a compound of claim 1.

32. A method of treating MMP-induced neoplastic disease states or cacer selected from the group consisting of leukemias, acute lymphoblastic, chronic lymphocytic, acute myeloblastic, chronic myelocytic, carcinomas and adenocarcinomas of the cervix, oesophagus, stomach, small intestines, colon, small cell lungs, breast and prostate, sarcomas, oesteroma, osteosarcoma, lipoma, liposarcoma, hemangioma, hemangiosarcoma, melanomas, amelanotic melanomas, melanotic melanomas, neoplasias, carcinosarcoma, lymphoid tissue type, follicullar reticulum, cell sarcoma and Hodgkin's Disease which comprises administering to the patient an effective matrix metalloproteinase inhibiting amount of a compund of claim 1.

33. A method of treating a smoking-induced emphysema in a patient thereof which comprises administering to the patient an effective matrix metalloproteinase inhibiting amount of a compound of claim 1.

\* \* \* \* \*